US006521232B1

(12) United States Patent
Fujita et al.

(10) Patent No.: US 6,521,232 B1
(45) Date of Patent: Feb. 18, 2003

(54) PROTEINS HAVING IMMUNOMODULATORY ACTIVITY AND REMEDIES FOR IMMUNOLOGICAL DISEASES

(75) Inventors: Koichiro Fujita, Tokyo (JP); Makoto Ohashi, Tokushima (JP); Shinjirou Imai, Saitama (JP)

(73) Assignee: Nisshin Flour Milling Co., Ltd., Tokyo (JP)

(*) Notice: Subject to any disclaimer, the term of this patent is extended or adjusted under 35 U.S.C. 154(b) by 0 days.

(21) Appl. No.: 09/647,514

(22) PCT Filed: Mar. 30, 1999

(86) PCT No.: PCT/JP99/01643

§ 371 (c)(1), (2), (4) Date: Sep. 29, 2000

(87) PCT Pub. No.: WO99/51633

PCT Pub. Date: Oct. 14, 1999

(30) Foreign Application Priority Data

Mar. 31, 1998 (JP) .......................................... 10-087189

(51) Int. Cl.$^7$ ......................... A61K 39/38; A61K 39/00

(52) U.S. Cl. ................................ 424/191.1; 424/185.1; 424/184.1; 530/350

(58) Field of Search ........................ 530/350; 424/184.1, 424/185.1, 191.1

(56) References Cited

FOREIGN PATENT DOCUMENTS

WO WO 93/23077 A 11/1993

OTHER PUBLICATIONS

Mol. Immunol. 30 [14] (1993) Owashi M. et al., Molecular Cloning and Characterization of a Novel Neutrophil Chemotactic Factor from a Filarial Parasite pp. 1315–1320.

Proc. Natl. Acad. Sci. U.S.A. 89 (1992) Poole C.B. et al., Cloning of a cutilar antigen that contains multiple tandem repeats from the filarial parasite Dirofilaria immitis pp. 5986–5990.

Mol. Biochem. Parasitol. 54 (1992) Culpepper J. et al., "Molecular characterization of a Dirofilaria immitis cDNA encoding a highly immunoreactive antigen" pp. 51–62.

JP 7–508031–A, (Colorado State University Research Foundation) Sep. 7, 1995.

J. Allergy Clin. Immunol. 95 [6] (1995) Lee T.D. et al., "IgE regulation by nematodes: the body fluid of Ascaris contains a B–cell mitogen", pp. 1246–1254.

Parasite Immunol. 17 [2] (1995) Inuo G. et al., Toxocara canis adult worm antigen induces proliferative response of healthy human peripheral blood mononuclear cells pp. 77–84.

Int. Arch. Allergy Immunol. 102 [2] (1993) "Potential of IgE responses to third–party antigens mediated by Ascaris suum Solube Products" pp. 185–190.

Owhashi et al Acession No. Q94509, Feb. 1997.*

Ngo et al., in The Protein Folding Problem and Tertiary Structure Prediction, 1994, Merz, et al., (ed.), Birkhauser, Boston, MA, pp. 433 and 492–495.*

Mikayama et al, Molecular cloning and functional expression of a cDNA encoding gycosylation–inhibting factor, Nov. 1993, Proc. Natl. Acad. Sci, USA vol. 90: 10056–10060.*

Voet et al., Biochemistry I, 1990, pp. 126–234.*

Attwood et al., The babel of bioinformatics, Oct. 2000, Science 290 (5491): 471–473.*

Skolnick et al., From genes to protein structure and function: novel applications of computational approaches in the genomic era, Jan. 2000, Trends in Biotech. 18(1): 34–39.*

* cited by examiner

*Primary Examiner*—Christina Chan
*Assistant Examiner*—Phuong N. Huynh
(74) *Attorney, Agent, or Firm*—Fish & Richardson P.C.

(57) ABSTRACT

The present invention provides a protein of the following formula (I) having immunomodulatory activity: X-Y-Z (I) wherein X represents an amino acid sequence of SEQ ID NO: 1 or 2, each of Y and Z is absent or represents an amino acid sequence of SEQ ID NO: 1 or 2. The above protein is derived from helminth and can be used to treat various immune diseases due to its immunomodulatory activity. The above protein can also be used to treat various allergic diseases due to is ability to stimulate the production of non-specific IgE.

1 Claim, 7 Drawing Sheets

PROTEINS HAVING IMMUNOMODULATORY ACTIVITY AND REMEDIES FOR IMMUNOLOGICAL DISEASES

This is a national stage application of PCT/US99/01643, filed Mar. 30, 1999.

FIELD OF THE INVENTION

The present invention relates to proteins having immunomodulatory activity and therapeutic agents for immune diseases. More specifically, the present invention relates to proteins derived from protein produced from helminth, which modulate the immune system in a host.

BACKGROUND OF THE INVENTION

Agents including steroids and immunosupressants, such as cyclosporine, have been used conventionally for treatment of autoimmune diseases, called intractable diseases, and allergic diseases. However, these agents have only symptomatic therapy and no effective agent exerting a markedly advantageous effect has been developed yet. Further, the steroids and cyclosporine have problems including strong side effects and drug resistance.

Recently, the dramatic advance of molecular biology and immunology has determined the detailed mechanism of immune system, various factors involved in this mechanism and receptors recognizing these factors, and has unfolded their functions and roles in the immune system. Examples of these factors include cytokines, such as various interleukins, receptors recognizing the cytokines, antibodies against the cytokines and receptors, adhesion molecules and antibodies against the adhesion molecules.

For treatment of autoimmune diseases and allergy, for example, many attempts have been made to use the above-mentioned factors as so-called "biopharmaceuticals" in the treatment where these diseases result from dysfunction of these factors.

However, these attempts are only directed to the treatment of factors functioning abnormally. These attempts therefore provide only a local immunological treatment and are considered to be an extension of conventional symptomatic treatments.

Accordingly, there is a need for a therapeutic agent based on new idea supported by the mechanism of immune system as a whole in order to cure the above intractable diseases completely.

On the other hand, parasitologists have found a tendency for patients infected with parasitic helminth to be less susceptible to allergy, based on the epidemiological correlation between helminth infection and allergy. They have also reported that patients with systemic lupus erythematosus exhibit ameliorated symptoms by parasitic infection.

However, some allergologists state that such an epidemiological correlation is groundless and absolutely unfounded because the tendency found by parasitologists has not been scientifically proved.

Regarding molecules derived from helminth, Fujita et al. has reported finding an allergen from *Dirofilaria immitis* (Fujita et al., 1979), and Horii et al. has found *Dirofilaria immitis* neutrophil chemotactic factor (DiNCF) and has determined its amino acid sequence (Horii et al., 1986). Further, C. B. Poole et al. has isolated DiNCF as Cuticular antigen produced from *Dirofilaria immitis* and has cloned its partial gene sequence, indicating that DiNCF has a structure in which the antigen molecules repeated in tandem (C. B. Poole, 1992).

The cDNA cloning of DiNCF has also been reported, for example, by J. Culpepper (J. Clupepper, 1992), Ohashi et al. (Ohashi et al., 1993), and C. B. Poole et al. (C. B. Peele et al., 1996).

These reports suggest nothing about the immunomodulatory activity of the helminth-produced molecules as defined in the present invention, because of focusing their attention only on neutrophil chemotactic activity and/or antigenicity of the molecules.

An extract of parasitic helminth has been already known to induce B cell proliferation. For example, a soluble molecule from *Ascaris suum* involved in IgE production (T. D. G. Lee et al., 1993), a crude antigen from *Toxocara canis* having the ability to increase human peripheral blood cells (Inuo et al., 1995) and an antigen from *Ascaris suum* having mitogenicity (T. D. G. Lee et al., 1995) have been reported.

However, each of these extracts was used without further isolation in each experiment, so that a single molecule isolated from the extracts has not been reported to induce B cell proliferation independently of T cells.

DISCLOSURE OF THE INVENTION

In view of the foregoing, there is still a lot of discussion among scientists of different fields and they have not reached a clear conclusion. We have focused our research effort on how the parasitic helminth infection affects the immune system in a host, and have proved that a molecule derived from parasitic helminth is effective in the treatment of immune diseases, and finally have completed the invention.

The present invention is based on the self-defense mechanism that parasites have attained over several hundreds of millions of years in order to protect themselves against immune response of their hosts. The present invention provides an agent designed according to this concept, i.e., a brand-new idea.

The present invention provides a protein of the following formula (I) having immunomodulatory activity:

$$X\text{-}Y\text{-}Z \qquad (I)$$

wherein X represents an amino acid sequence of SEQ ID NO: 1 or 2, each of Y and Z is absent or represents an amino acid sequence of SEQ ID NO: 1 or 2.

The present invention also provides the following recombinant protein (a) or (b):

(a) a protein having an amino acid sequence selected from SEQ ID NO: 7–14; and (b) a protein having an amino acid sequence selected from SEQ ID NO: 7–14 in which one or more amino acids are deleted, substituted or added, and having immunomodulatory activity.

The present invention also provides the following recombinant protein (a) or (b):

(a) a protein having an amino acid sequence of SEQ ID NO: 15; and (b) a protein having an amino acid sequence of SEQ ID NO: 15 in which one or more amino acids are deleted, substituted or added, and having immunomodulatory activity.

The present invention further provides an immunomodulating agent comprising the following recombinant protein (a) or (b):

(a) a protein having an amino acid sequence selected from SEQ ID NO: 1–6; and (b) a protein having an amino acid sequence selected from SEQ ID NO: 1–6 in which one or more amino acids are deleted, substituted or added, and having immunomodulatory activity.

The present invention further provides a therapeutic agent for immune diseases, which comprises one or more proteins described above as an active ingredient.

The immune disease includes autoimmune diseases, in particular, Th1-dominant autoimmune diseases selected from the group consisting of multiple sclerosis, insulin-dependent diabetes mellitus, Crohn's disease, uveitis, chronic rheumatism, and systemic lupus erythematosus.

The immune disease also includes autoimmune diseases not known to be Th1-dominant, which are selected from the group consisting of scleroderma, multiple myositis, vasculitis syndrome, mixed connective tissue disease, Sjögren's syndrome, hyperthyroidism, Hashimoto's disease, myasthenia gravis, Guillain-Barré syndrome, autoimmune hepatopathy, ulcerative colitis, autoimmune nephropathy, autoimmune hematopathy, idiopathic interstitial pneumonia, hypersensitivity pneumonitis, autoimmune dermatosis, autoimmune cardiopathy, autoimmune infertility, and Behcet's disease.

The present invention also provides an agent for stimulating IgE production, which comprises one or more proteins described above as an active ingredient. The present invention further provides a therapeutic agent for allergic diseases, which comprises one or more proteins described above as an active ingredient.

The allergic disease includes chronic bronchitis, atopic dermatitis, pollinosis (allergic rhinitis), allergic angiitis, allergic conjunctivitis, allergic gastroenteritis, allergic hepatopathy, allergic cystitis, and allergic purpura.

The present invention also provides an immunomodulating agent which comprises one or more proteins described above as an active ingredient. The immunomodulating agent may modulate rejection reaction occurring in organ transplantation.

The present invention also provides an immunomodulation method which comprises administering one or more proteins described above in an effective amount to a patient in need of such treatment.

The present invention also provides a method for treating immune diseases, which comprises administering one or more proteins described above in an effective amount to a patient in need of such treatment.

The present invention also provides a method for stimulating IgE production, which comprises administering one or more proteins described above in an effective amount to a patient in need of such treatment.

The present invention also provides a method for treating allergic diseases, which comprises administering one or more proteins described above in an effective amount to a patient in need of such treatment.

The present invention also relates to the use of one or more proteins described above in the production of immunomodulating agents.

The present invention also relates to the use of one or more proteins described above in the production of therapeutic agents for immune diseases.

The present invention also relates to the use of one or more proteins described above in the production of IgE production-stimulating agents.

The present invention also relates to the use of one or more proteins described above in the production of therapeutic agents for allergic diseases.

The present invention will be further described below.

As used herein, "immunomodulatory activity" means stimulation of non-specific immunoglobulin production from B cells and modulation of immune responses mediated by Th1 and Th2.

As used herein, "stimulation of non-specific immunoglobulin production from B cells" means that B cells are stimulated to produce non-specific immunoglobulins (Ig), particularly non-specific IgE, not to produce immunoglobulins against specific antigens. When producing Ig, in general, B cells should be converted into blast cells (i.e., blast formation) upon stimulation by antigen-presenting cells which present specific antigens on their surface. However, the proteins of the present invention do not cause the blast formation, so that mature B cells proliferate and thus produce non-specific Ig.

As used herein, "modulation of immune responses mediated by Th1 and Th2" means that the immune response pattern is changed from cellular immunity into humoral immunity and vice versa by inhibiting cytokine production from each T cell subset Th1 and Th2 or by inducing cytokines from one subset that inhibit cytokines produced from the other subset.

As used herein, "immune disease" refers to a disease resulting from dysfunction of the immune system, one of defense mechanisms in the body, including diseases caused by both abnormal humoral and cellular immunity. This term also includes autoimmune diseases caused by autoantibody, autosensitized lymphocyte or immune complex, as well as graft versus host disease caused by graft versus host reaction (GVH reaction) in which graft rejection occurs. Allergic diseases and the like are also included.

As used herein, "Th1-dominant autoimmune disease" refers to an autoimmune disease showing increased cytokine production from Th1 cells, including IFN-$\gamma$, IL-2, GM-CSF, TNF-$\alpha$, and IL-3. Specific examples include multiple sclerosis, insulin-dependent diabetes mellitus, Crohn's disease, uveitis, chronic rheumatism, and systemic lupus erythematosus.

As used herein, "autoimmune disease not known to be Th1-dominant" refers to an autoimmune disease that is not known to show increased cytokine production from Th1 cells. Specific examples include scleroderma, multiple myositis, vasculitis syndrome, mixed connective tissue disease, Sjögren's syndrome, hyperthyroidism, Hashimoto's disease, myasthenia gravis, Guillain-Barrésyndrome, autoimmune hepatopathy, ulcerative colitis, autoimmune nephropathy, autoimmune hematopathy, idiopathic interstitial pneumonia, hypersensitivity pneumonitis, autoimmune dermatosis, autoimmune cardiopathy, autoimmune infertility, and Behcet's disease.

As used herein, "allergic disease" refers to a disease associated with allergic reaction. Specific examples include chronic bronchitis, atopic dermatitis, pollinosis (allergic rhinitis), allergic angiitis, allergic conjunctivitis, allergic gastroenteritis, allergic hepatopathy, allergic cystitis, and allergic purpura.

As used herein, "deletion, substitution or addition of one or more amino acids" or "one or more amino acids are deleted, substituted or added" means both naturally occurring modification and artificially introduced modification using site-directed mutagenesis (Nucleic Acids Research, Vol. 10, No. 20, pp. 6487–6500, 1982) etc.

The immunomodulatory proteins of the present invention have the above formula (I): X-Y-Z. In the formula, X represents an amino acid sequence of SEQ ID NO: 1 or 2, each of Y and Z is absent or represents an amino acid sequence of SEQ ID NO: 1 or 2. The amino acid sequence of SEQ ID NO: 1 is hereinafter designated V1, while the amino acid sequence of SEQ ID NO: 2 is designated V2.

When expressed using V1 and V2, the proteins of the present invention encompass V1 (SEQ ID NO: 1), V2 (SEQ ID NO: 2), V1+V2 (SEQ ID NO: 3), V2+V1 (SEQ ID NO: 4), V1+V2+V1 (SEQ ID NO: 5), V2+V1+V2 (SEQ ID NO: 6), V1+V1 (SEQ ID NO: 7), V2+V2 (SEQ ID NO: 8), V1+V1+V1 (SEQ ID NO: 9), V1+V1+V2 (SEQ ID NO: 10), V1+V2+V2 (SEQ ID NO: 11), V2+V2+V2 (SEQ ID NO: 12), V2+V2+V1 (SEQ ID NO: 13), and V2+V1+V1 (SEQ ID NO: 14).

The amino acid sequence homology between V1 and V2 is relatively high, and amino acids 1–61 in these sequences are homologous to each other. This homologous sequence is shown in SEQ ID NO: 15.

Each of V1 and V2 of the present invention is protein originated from *Dirofilaria immitis,* a kind of parasitic helminth. The protein from *Dirofilaria immitis* may be obtained by combining the following techniques: extraction of proteins from *Dirofilaria immitis,* anion exchange chromatography, and gel filtration chromatography etc.

The protein from *Dirofilaria immitis,* hereinafter designated DiNCF, has neutrophil chemotactic activity and comprises a repeated sequence in which two types of tens of molecules DiNCF V1 and DiNCF V2 are repeated in tandem. Ohashi et al. have cloned cDNA for DiNCF (Ohashi, supra) and thus amino acid sequences for DiNCF V1 and DiNCF V2 have been determined.

These amino acid sequences correspond to V1 and V2, respectively. V1 contains 129 amino acids, while V2 contains 131 amino acids (SEQ ID NO: 1 and 2).

The proteins of the present invention may encompass heterodimer and heterotrimer, in which V1 and V2 are repeated in tandem, as well as homodimer and homotrimer, in which one of V1 or V2 is repeated in tandem. The homodimer and homotrimer are both non-naturally occurring proteins.

In these two proteins, their N-terminal sides, i.e., amino acids 1 to 61 are homologous to each other, but the rest of amino acids are less homologous to each other.

The proteins of the present invention may encompass not only proteins having full-length sequences of V1 and V2, but also a protein having the amino acid sequence of SEQ ID NO: 15.

The amino acid sequence of SEQ ID NO: 15 corresponds to amino acids 1–61 of V1 and V2, and may be modified by substitution, deletion or addition of one or more amino acids so long as the resulting protein has immunomodulatory activity.

Further, preferred amino acid sequences comprise amino acids 1–76 of the amino acid sequence depicted in SEQ ID NO: 1 or 2.

These amino acid sequences may be modified by substitution, deletion or addition of one or more amino acids in the same manner for the protein having the amino acid sequence of SEQ ID NO: 15.

To obtain a gene encoding the protein of the present invention, a vector carrying DiNCF gene may be subjected to PCR method using primers, each of which includes an appropriate restriction site, to amplify the gene of interest; the vector may be treated with an appropriate restriction enzyme to isolate a DNA fragment having the desired molecular weight, which may be then ligated to an appropriate linker; or each DNA encoding DiNCF V1 or DiNCF V2 may be chemically synthesized based on the nucleotide sequence of the gene encoding *Dirofilaria immitis* protein according to standard techniques and these DNAs may then be optionally joined to one another to form the sequences listed above.

The DNA fragment thus obtained, i.e., the gene encoding the protein of the present invention, may be ligated to an appropriate vector treated with a restriction enzyme to obtain a recombinant vector for protein expression.

This recombinant vector may be used to transform an appropriate host. The desired transformant may be selected and then grown to obtain a vector producing the protein of interest.

Examples of the vector carrying DiNCF gene include vectors pDi6, pDi18 and pD-4 that carry the nucleotide sequences of DNAs encoding DiNCF V1 and DiNCF V2, each of which has been constructed simultaneously with clone pD-4 constructed for the purpose of cloning DiNCF (see Maruyama, H. et al., 30 (14): 1315–1320, 1993). The vector pDi6 may be preferably used because it contains both V1 and V2 genes.

The vector pDi6 was constructed according to the method described in Ohashi (Ohashi M. et al., Mol. Immunol. 30 (14):1315–1320, 1993). Namely, adult *Dirofilaria immitis* is collected from the heart of a dog naturally infected with *Dirofilaria immitis* and cut into small pieces on ice, from which mRNA is then purified using mRNA Purification Kit (Pharmacia).

cDNA is synthesized from this mRNA using cDNA Synthesis Kit (Pharmacia) and then inserted into an EcoR I site of λgt11 vector (Promega Biotec., Madison, Wis., USA). DNA of this cDNA-inserted λgt11 is subjected to in vitro packaging using Gigapack (Stratagene, La Jolla, Calif., USA) to construct a cDNA library.

The clone of interest is selected from this cDNA library using an anti-DiNCF antibody according to the method described in Huynh, T. V. et al., A Practical Approach, Vol. 1, pp. 49–78, Glover D. M. ed., IRL Press, Oxford.

The selected clone is digested with EcoR I to excise the inserted gene from the phage DNA. The excised gene is then inserted into EcoR I site of phagemid vector pBluescript SK (−) to construct the plasmid pDi6.

To obtain a DNA, e.g., V1+V2, in which these genes are repeated in tandem, restriction enzyme NspV may be preferably used because the consensus sequence has only one site for this enzyme to recognize.

Alternatively, the chemical synthesis of the above DNA fragment may be carried out in a known manner such as phosphoramidite method or phosphit-triester method.

The vector used for construction of the recombinant vector for protein expression includes plasmid vectors such as pET3a, pTrc and pKK2B-3; phage vectors such as λgt11 and M13; pBluescript II; or phagemid vectors such as pcDNA2.1. The plasmid vector pET3a may be preferably used because it leads to good yield.

The host to be transformed includes *E. coli* and the like. *E. coli* may be preferably used because of its simple manipulation, particularly HMS 174 (DE3) strain may provide a high protein expression efficiency.

The host may be transformed using standard techniques including, but not limited to, calcium chloride method or electroporation method, both of which are preferred due to their high transformation efficiency.

The transformants obtained by transformation with the vector carrying the gene encoding the protein of the present invention may be screened for their antibiotic resistance. The antibiotic used as a screening marker includes ampicillin, tetracycline, kanamycin and the like. Ampicillin may be preferably used because the preferred vector is pET3a.

The selected transformant may be grown to obtain the protein of the present invention.

The DNA fragment having the nucleotide sequence encoding the protein of the present invention may be modified by site-directed mutagenesis to introduce a mutation at any position in the DNA fragment. Such a DNA modification can provide various modified proteins.

The present invention will be further described in terms of sequence V1.

Plasmid vector pDi6 carrying a gene encoding DiNCF V1 region (distributed from Prof. Makoto Ohashi of Tokushima University) is used as a template. PCR amplification is carried out using this template vector and primers, each including a restriction site and a stop codon. By using such a primer including a restriction site, the fragment of interest can be introduced into an expression vector downstream from its initiation codon in the desired orientation and in frame. This enables the protein of interest to be expressed.

The use of the following primers achieve an efficient amplification of the nucleotide sequence of interest:

N-terminal primer:

5'-GCATATGAATGATCATAATTTAGAAAGC-3' (SEQ ID NO: 16), and

C-terminal primer:

5'-CTAAAGGATCCTATCACCGCTTACGCCGTT CATTCATTG-3' (SEQ ID NO: 17).

These primers may be chemically synthesized, for example, by phosphoramidite method, or we may ask a company (e.g. Biologica Co.) to synthesize these primers.

PCR may be carried out using the above primers, DiNCF V1 as a template, Ex Taq DNA polymerase, and a buffer and dNTP (equivalent mixture of dATP, dGTP, dCTP, dTTP) contained in Ex Taq Kit (Takara Shuzo Co., Ltd.) etc.

The resulting amplified fragment may be purified by MicroSpin Column and the like, digested with Nde I and BamH I, purified again, and then inserted into an expression vector. For this purpose, pET3a is digested with Nde I and BamH I and purified using MicroSpin Column S400 (Pharmacia) to obtain its main segment as an expression vector.

The above PCR amplified fragment is ligated to this digested pET3a using DNA ligation kit (Takara Shuzo Co., Ltd.) according to the manufacture's instructions to obtain the circular DNA of interest.

The circular DNA is introduced into *E. coli* strain JM109 by calcium chloride method to transform the strain JM109. The resulting transformants are cultured in LB medium with ampicillin. Cells grown in the medium are collected by centrifugation and subjected to alkaline SDS method to isolate and obtain a plasmid, designated pDP5.

The nucleotide sequence of the resulting plasmid may be examined using Sequenase kit (United States Biochemical Corporation, USA) in order to confirm whether the insert of interest is inserted correctly in the vector and whether any unexpected changes are observed before and after the insert.

To obtain the dimer or trimer protein of the present invention, an expression vector may be constructed as described below in terms of dimer V1+V1.

The plasmid pDP5 constructed as described above is digested with Nsp V, treated with phenol by standard techniques, dephosphorylated using calf intestine alkaline phosphatase (CIP), and then treated with phenol in order to deactivate the enzyme.

Meanwhile, the plasmid pDi6 is digested with the same restriction enzyme and electrophoresed on agarose gel to purify a band of the desired molecular weight. GENECLEAN II kit (Funakoshi Co., Ltd.) etc. may be used for this purpose.

This purified fragment is ligated to the linearized vector treated with CIP in the same manner as described above. The ligated DNA is used to transform *E. coli* strain JM109 to obtain transformants.

The transformed clones are picked up properly and cultured overnight in a medium with ampicillin. Cells grown in the medium are collected by centrifugation, from which vector DNAs are then isolated and purified by alkaline SDS method. Each of the vectors thus obtained is digested with an appropriate restriction enzyme and analyzed by electrophoresis to obtain the vector of interest.

This vector is used to transform *E. coli* HMS 174 (DE3) in the same manner as described above. Each of the resulting transformants is cultured until the absorbance $A_{550}$ becomes 0.8. When the absorbance $A_{550}$ becomes 0.8, the culture further continues with addition of IPTG (isopropylthiogalactoside).

The cells are separated from the culture fluid by centrifugation, suspended in a solution containing 8M urea and 0.1M Tris-HCl (pH 7.0), and then ultrasonically treated and centrifuged to obtain the supernatant.

This supernatant is subjected to SDS polyacrylamide electrophoresis using Phast System (Pharmacia). A control is *E. coli* strain transformed with normal pET3a.

The production of the desired protein can be confirmed by the above procedures.

Each of the transformants thus obtained is cultured and grown cells are collected by centrifugation. A predetermined amount of the cells is extracted with hydrochloric acid to obtain a hydrochloric acid extract.

After neutralization with sodium hydroxide, this extract is mixed with ammonium sulfate and centrifuged to separate precipitated products. These precipitated products are dissolved in PBS (physiological phosphate buffer) and purified by gel filtration chromatography to obtain the final purified product.

The proteins thus obtained can also be used to prepare DNAs having nucleotide sequences encoding these proteins according to various known techniques. In the present invention, DNAs having these nucleotide sequences may be modified to introduce substitution, deletion, addition or insertion of one or more bases, for example, according to site-directed mutagenesis (Zoller et al., Nucleic Acids Research, Vol. 10, No. 20, pp. 6487–6500, 1982). Those skilled in the art may easily prepare these modified DNAs. The present invention can encompass these DNAs so long as proteins encoded by them have immunomodulatory activity.

Physiological functions of these proteins may be examined as follows. A mouse is sacrified by dislocating its cervical vertebra and its spleen is excised to obtain lymphocytes. These splenic lymphocytes are centrifuged to remove the supernatant, washed with ACT solution (0.83% $NH_4Cl$, 170 mM Tris-HCl (pH 7.6)), and then suspended in RPMI 1640 medium with fetal calf serum (FCS) to form splenic lymphocyte suspension.

Next, B cells are prepared as follows. These splenic lymphocytes are incubated with an anti-Thy-1.2 antibody added thereto at 4° C., and then suspended in RPMI 1640 medium with 5% fetal calf serum (FCS) after washing. This suspension is mixed well and reacted with a commercially available complement solution prepared from rabbit etc. at about 37° C. for about one hour. After washing, these lymphocytes are suspended again in RPMI 1640 medium with 5% FCS at a predetermined cell density (B cell suspension). The cell density suitable for proliferative response to stimulation is $1\times10^5$ cells/mL to $5\times10^6$ cells/mL.

The proliferative response to stimulation may be confirmed as follows.

The B cell suspension prepared as described above is divided into each well of a 24-well plate and cultured in RPMI 1640 medium with 5% FCS for a predetermined period. Each protein of the present invention is added at a predetermined concentration and the culture continues for additional 48 hours in order to perform MTT assay. The protein of the preset invention is used preferably at a concentration of 0.1 to 1,000 μg/nL because this concentration range provides a significant response in MTT assay, more preferably 10 to 100 μg/mL because a higher response can be observed.

MTT assay may be performed as follows. The cell suspension (500 μl) is incubated and reacted with MTT solution (50 μl) added thereto at 37° C. for 4 hours, and then incubated with stop solution (450 μl) added thereto at room temperature for 30 minutes in order to stop the reaction. Absorbances at 630 nm and 570 nm (designated $A_{630}$ and $A_{570}$, respectively) are measured to determine the grade of proliferative response.

The MTT solution is prepared by dissolving MTT (3-[4, 5-dimethylthiazol-2-yl]-2,5-diphenylterazolium bromide, Sigma) in PBS at a concentration of 5 mg/mL. The stop solution is isopropanol containing 0.04 N hydrochloric acid.

For a blank experiment, the medium alone is subjected to the same treatment as described above and tested for its absorbances at 630 nm and 570 nm (designated $A0_{630}$ and $A0_{570}$, respectively). MTT assay value can be calculated based on these measured values using the following equation:

$$MTT \text{ assay value}=(A_{570}-A_{630})-(A0_{570}=A0_{630}).$$

Lipopolysaccharide (LPS) may be used as a positive control.

Each of the peptides according to the present invention may be tested for its ability to induce IgE production as follows. For example, a mouse is administered intraperitoneally with a mixture of DiNCF V1 in a predetermined amount and aluminum hydroxide adjuvant (ALUM).

Blood is taken from its caudal artery with a heparinized tube before administration and on the 7th, 14th and 21st days after administration. Plasma is separated and IgE contained therein is detected by enzyme antibody technique. Enzyme antibody technique may be carried out according to, but not limited to, the following procedures.

The following materials are used in this technique: anti-DNP IgE as a standard IgE, anti-mouse IgE Fc ϵ rat monoclonal antibody as a primary antibody, peroxidase-labeled anti-mouse IgE polyclonal antibody as a secondary antibody, an appropriate blocking agent, reaction buffer such as PBS containing 0.1% bovine serum albumin, and PBS-Tween containing 0.05% Tween 20 in PBS.

The primary antibody is diluted with sodium carbonate buffer (pH 9.5) to a predetermined concentration and bound to the surface of each well in a 96-well microtiter plate. Each well is blocked using blocking solution and then washed with PBS-Tween.

The protein of the present invention or the standard IgE is added to each well, for example, in an amount of 100 μL/well, and incubated at room temperature for an appropriate period, e.g., 3 hours. The plate is washed with PBS-Tween 2 or 3 times. The secondary antibody is optionally diluted with the reaction buffer and added to each well in an amount of 100 μL/well. Incubation continues at room temperature for about 3 hours. The plate is washed with PBS-Tween.

Substrate solution is then added to each well and incubated in the dark for a few minutes to develop color. Upon development of a detectable color, stop solution is added to each well. The plate is then read at 490 nm using a microplate reader to calculate the concentration of IgE contained in plasma based on calibration curve prepared from the standard IgE.

Each peptide may be tested for its in vivo immunomodulatory activity using a rat model with autoimmune encephalomyelitis.

Namely, the protein of the present invention is administered to a rat via the footpads of its hind legs in an amount of 10 to 1,000 μg/rat, preferably 100 μg/rat. Control group is similarly administered with PBS. This administration continues for 41 days. On the 41st day after the administration has started, both test and control groups are further administered with guinea pig myelin basic protein peptide (GPE) emulsified with an appropriate adjuvant in an amount of about 2 to 10 μg/rat, preferably 5 μg/rat. Preferred adjuvants include killed Mycobacterium tuberculosis and the like.

On the 14th day after the GPE administration, changes in clinical signs of both groups are scored in accordance with the following criteria shown in Table 1.

TABLE 1

Criteria for scoring clinical signs

| Score | Clinical signs |
|---|---|
| 0 | normal |
| 1 | no paralysis, but less active and moving slowly |
| 2 | light paralysis, showing abnormal standing reflex* |
| 3 | observable paralysis in hind legs, unsteady walking |
| 4 | complete paralysis in hind legs, but movable front legs |
| 5 | complete paralysis in all legs, agonal stage |
| 6 | death |

*Abnormal standing reflex means that a test animal fails to stand up immediately when inverted, or that a test animal fails to hold its tail up when its tail is lifted and then released.

Each protein of the present invention tested for its immunomodulatory activity may be formulated with each pharmaceutically acceptable ingredient to form a therapeutic agent for immune diseases. The pharmaceutically acceptable ingredient includes excipient, binder, disintegrating agent, coloring agent, flavoring agent, corrective, solubilizing agent, emulsifying agent, preservative, suspending agent, stabilizing agent, isotonizing agent, and buffer.

Specifically, the excipient includes starch or lactose for solid formulation, and water for liquid formulation. The binder includes gum Arabic, starch, carboxymethylcellulose sodium (CMC-Na), water, ethanol, and simple syrup. The disintegrating agent includes various surfactants, carbonate or the like. The coloring agent includes natural ones and synthetic ones acceptable under Food Sanitation Law.

The flavoring agent includes various essential oils such as orange oil, lemon oil and coriander oil. The corrective includes simple syrup and saccharose. The solubilizing agent includes polyoxyethylene hydrogenated castor oil derivatives, sodium benzoate and ethylenediamine.

The emulsifying agent includes various types of Span such as Span 20 and Span 60, various types of Tween such as Tween 20 and Tween 80. The preservative includes phenol, thimerosal and chlorobutanol.

The suspending agent includes CMC-Na, methylcellulose, simple syrup and glycerine. The stabilizing agent includes albumin, gelatin and sorbitol.

The isotonizing agent includes glucose and sodium chloride. The buffer includes phosphates.

These ingredients may be used alone or in combination for formulation.

The peptide of the present invention may be formulated in any dosage form including, but not limited to, tablet, granule, capsule, injection or the like.

Since the protein of the present invention affects T cell subset, Th2, as described above, immune diseases that can be treated using the therapeutic agent for immune diseases may be not only those thought to be Th1-dominant, but also those not known to be Th1-dominant. Specifically, the immune diseases thought to be Th1-dominant include multiple sclerosis, insulin-dependent diabetes mellitus, Crohn's disease, uveitis, chronic rheumatism, and systemic lupus erythematosus.

The immune diseases not known to be Th1-dominant include scleroderma, multiple myositis, vasculitis syndrome, mixed connective tissue disease, Sjögren's syndrome, hyperthyroidism, Hashimoto's disease, myasthenia gravis, Guillain-Barrésyndrome, autoimmune hepatopathy, ulcerative colitis, autoimmune nephropathy, autoimmune hematopathy, idiopathic interstitial pneumonia, hypersensitivity pneumonitis, autoimmune dermatosis, autoimmune cardiopathy, autoimmune infertility, and Behcet's disease.

The protein of the present invention may also be used as an IgE production-stimulating agent for treatment of allergic diseases. That is, it enables mature B cells, i.e., polyclonal B cells to proliferate, thereby inducing increased non-specific IgE production, but not inducing monoclonal IgE production through blast formation as usually observed during elevation of IgE level.

When the protein of the present invention is used as an IgE production-stimulating agent, allergic diseases to be treated include chronic bronchitis, atopic dermatitis, pollinosis (allergic rhinitis), allergic angiitis, allergic conjunctivitis, allergic gastroenteritis, allergic hepatopathy, allergic cystitis, and allergic purpura.

The IgE production-stimulating agent comprising the protein of the present invention may also be used for treatment of rejection reaction occurring in organ transplantation. As used herein, "organ transplantation" refers to transplantation of organs including kidney, liver, lung and heart. Other organs such as bone, skin and tendon may also be included. The IgE production-stimulating agent of the present invention can alleviate rejection reaction occurring after the organ transplantation because it stimulates the production of non-specific IgE.

A formulation example is shown below using V1+V1 among the proteins of the present invention.

(Injection Formulation)

10 mM phosphate buffer (9 mL, pH 7.4) as a buffer and human serum albumin (10 mg) as a stabilizing agent were added to and dissolved in 1 mg/mL V1+V1 solution. The resulting solution was dispensed 1 mL into 5 mL glass vials.

V1+V1 0.1 mg

Phosphate buffer 0.9 mL

Human serum albumin 1 mg

Each vial was lyophilized at −20° C. and then sealed to obtain injection formulation. When used, this injection formulation may be reconstituted with 1 mL of distilled water for injection (Otsuka Pharmaceutical Co., Ltd.).

This specification includes part or all of the contents as disclosed in the specification and/or drawings of Japanese Patent Application No. 10-87189, which is a priority document of the present application.

BEST MODES FOR CARRYING OUT THE PRESENT INVENTION

The present invention will now be described in more detail but not limited thereto.

EXAMPLE 1

Preparation of *E.coli* Strain producing DiNCF that is a protein derived from *Dirofilaria immitis*

Figure 1:
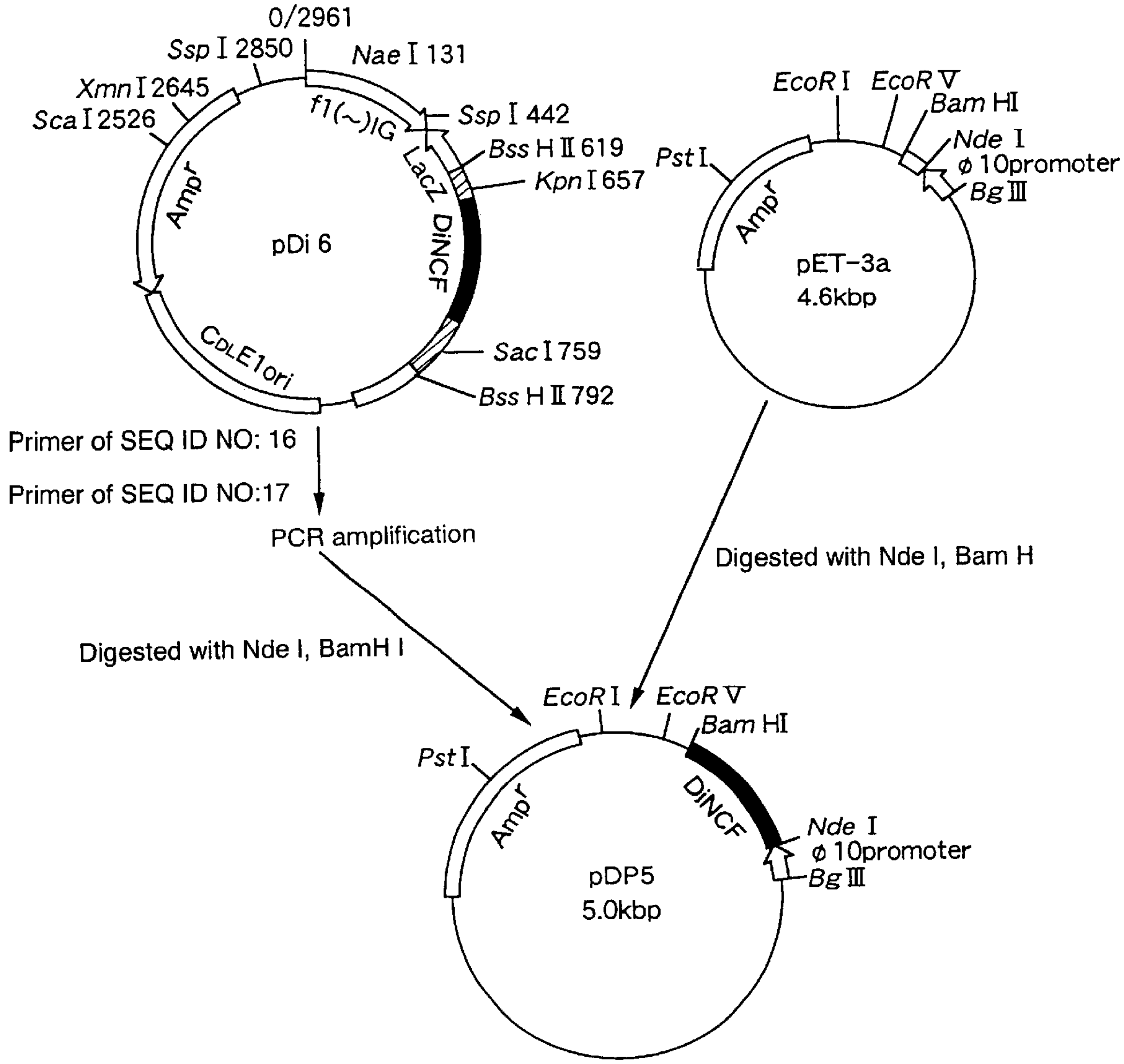
FIG. 1 shows the construction of the vector pPD5 for expressing the protein according to the present invention.
Figure 2:
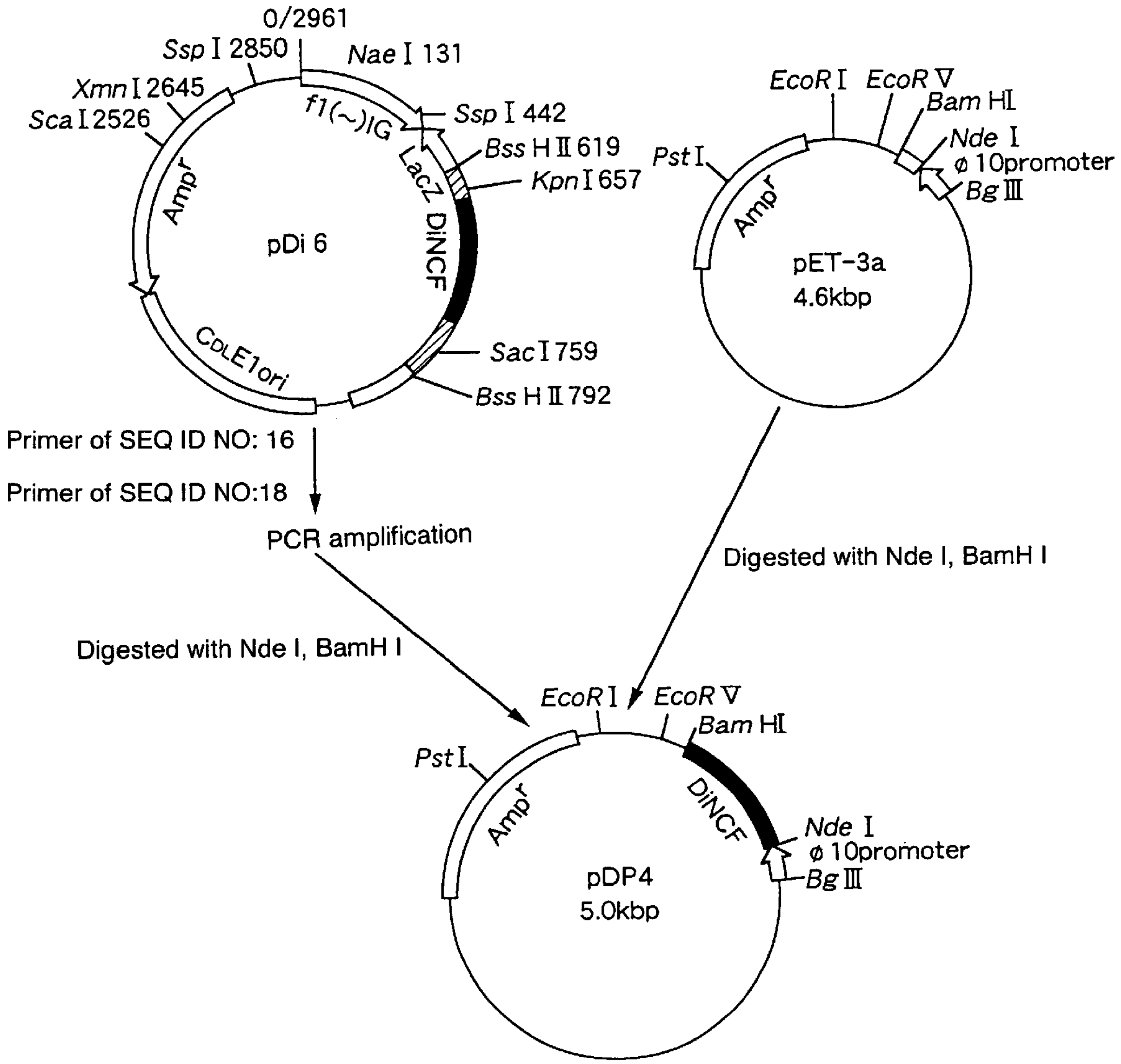
FIG. 2 shows the construction of the vector pPD4 for expressing the protein according to the present invention.
Figure 3:
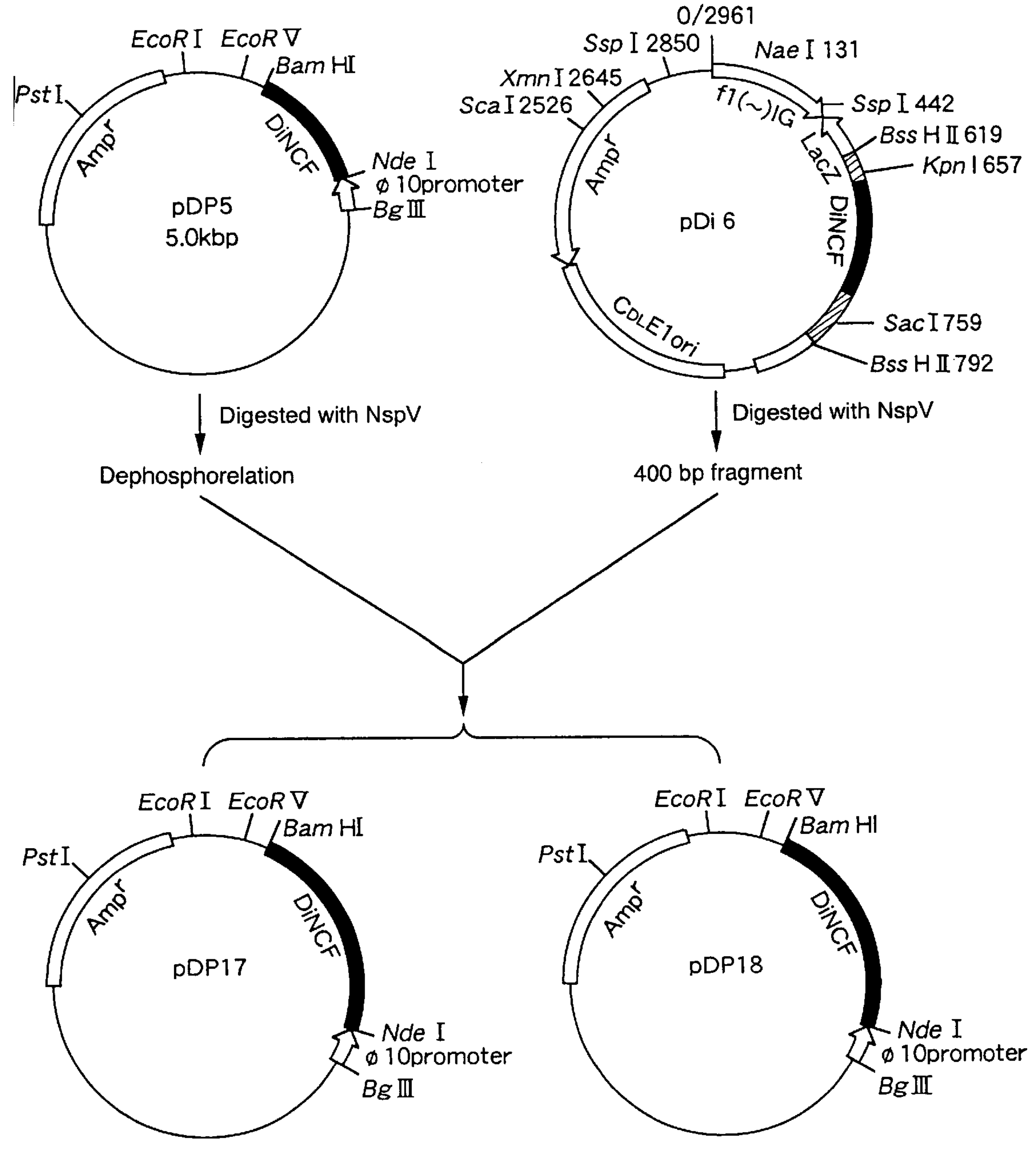
FIG. 3 shows the construction of the vectors pPD17 and pPD18 for expressing the proteins according to the present invention.
Figure 4:
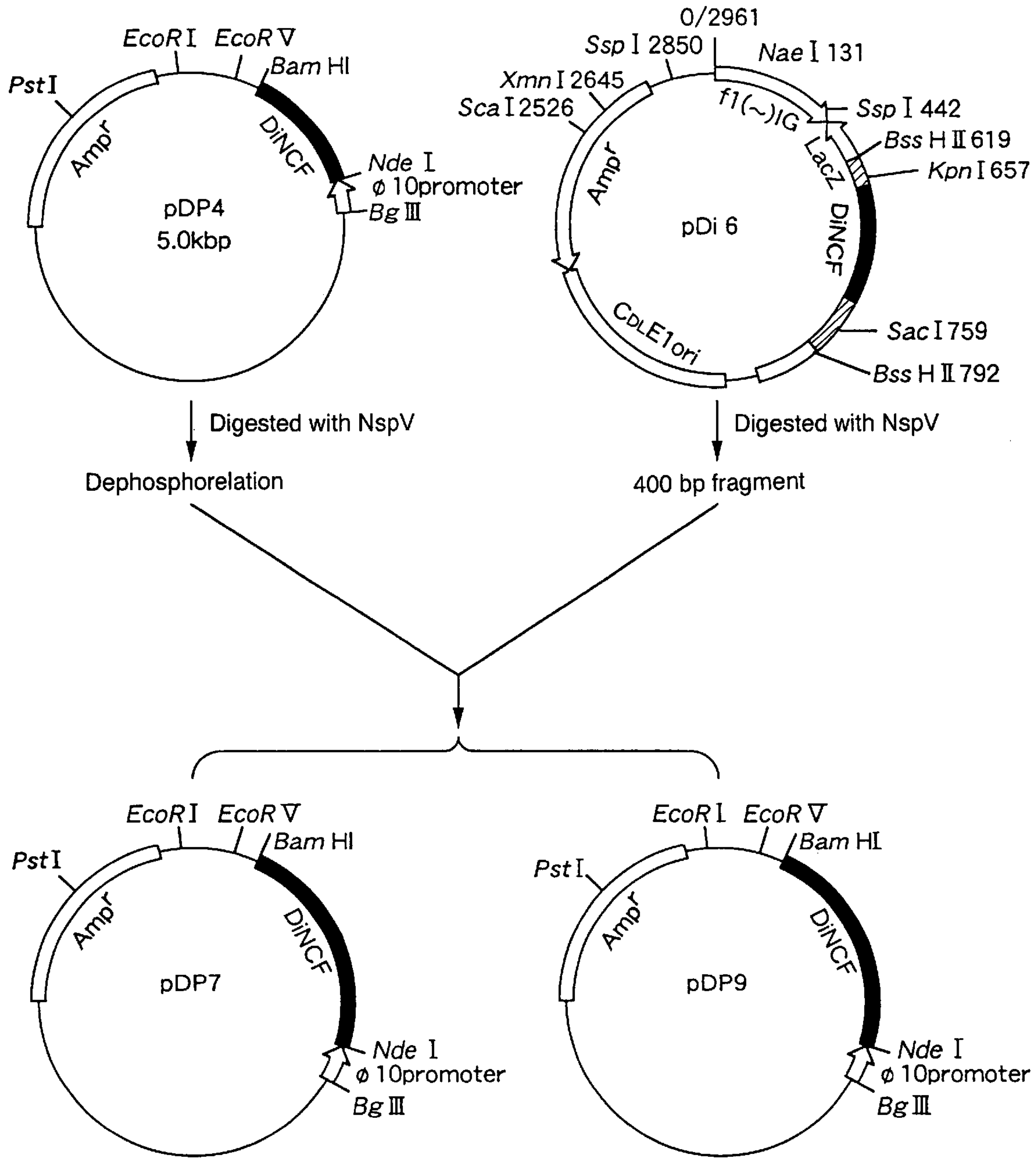
FIG. 4 shows the construction of the vectors pPD7 and pPD9 for expressing the proteins according to the present invention.
Figure 5:
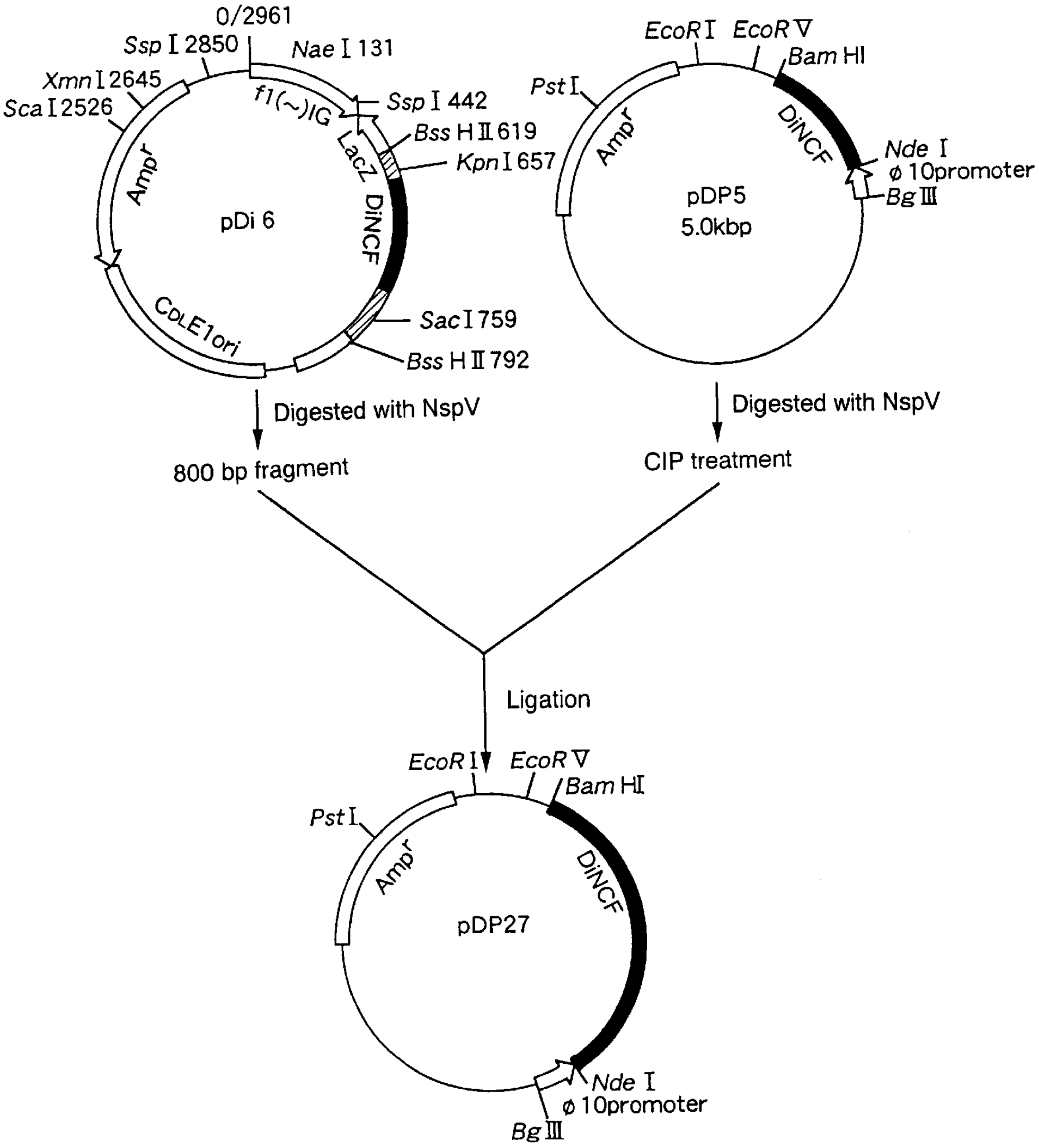
FIG. 5 shows the construction of the vector pPD27 for expressing the protein according to the present invention.

A vector pDP5, DiNCF V1 expression plasmid vector, was constructed as follows (FIG. 1).

A pDi6 was constructed according to the method of Ohashi (Ohashi M. et al., Mol. Immunol. 30(14):1315–1320 (1993)). 100 mg of adult worms were collected from the heart of a dog that has naturally been infected with *D. immitis,* washed with physiological saline, and cut into small pieces on ice. mRNA was purified using mRNA Purification Kit (Pharmacia) from these pieces.

Using this mRNA, cDNA was synthesized using cDNA Synthesis Kit (Pharmacia). The cDNA was inserted into an EcoR I site of λgt11 vector (Promega Biotec., Madison, Wis., USA). 5 μg of DNA of this cDNA-inserted λgt11 was packaged in vitro using Gigapack (Stratagene, La Jolla, Calif., USA), constructing a cDNA library.

The clone of interest was selected from this cDNA library as follows. The blood of a dog infected with *D. immitis* was diluted at a ratio of 1:1000 with 50 mM sodium carbonate buffer (pH 9.5). Using anti-DiNCF antibodies collected from this dilution, the clone of interest was selected from $2\times10^5$ clones by the method of Huynh et. al., (Huynh, T. V. et al., A Practical Approach, Vol. 1, pp.49–78, Glover D. M. ed., IRL Press, Oxford).

For example, the antibodies were bound to the surface of a plastic petri dish, and the dish was blocked using such as a block A (Dainippon Pharmaceutical Co., Ltd.). Phages were suspended in a solution containing a 10-fold dilution of the block A to form lysates. The resulting lysates were added to the petri dish and incubated for 2 hours at 37° C. After the petri dish was washed with PBS containing 0.1% Tween 20, 100 mM triethyl amine was added to the petri dish so that phages were eluted.

The phages obtained as described above were infected with *E. coli* again, then the phages were allowed to proliferate together with *E. coli.* This manipulation was repeated for several times, selecting positive clones.

10 μg of the selected clones were digested with 100 U/μL EcoR I so that 0.1 μg of DiNCF, a portion of genes to be inserted, was cut out of the phage DNA. 1 μg of a phagemid vector pBluescript SK(−) was digested with 10 U/μL of EcoR I. The 0.1 μg of DiNCF gene cut as described above was inserted into the EcoR I site of this digested phagemid vector, constructing a plasmid pDi6.

(1) Amplification of DINCF V1 Region with a Restriction Enzyme Cleavage Site Added The DiNCF V1 region was amplified by PCR using the pDi6 as a template and the following two primers:

N-terminal primer:

5'-GCATATGAATGATCATAATTTAGAAAGC-3' (SEQ ID NO: 16) and

C-terminal primer:

5'-CTAAAGGATCCTATCACCGCTTACGCCGTT CATTCATTG-3' (SEQ ID NO:17)

The two primers were obtained by asking Biologica CO., LTD. for the synthesis.

PCR was performed using PROGRAM TEMP CONTROL SYSTEM PC-700 (ASTEC CO., LTD) under the following condition.

0.5 $\mu$L of five units of Ex Taq DNA polymerase (Takara Shuzo Co.,Ltd) and the above primers dissolved with distilled water to 25 nmol/ml were used. Buffer, substrates and others attached to Ex Taq™ (Takara Shuzo Co., Ltd) were used.

Template DNA: pDi6 (distributed from Prof. Makoto Ohashi of Tokushima University) was used at a concentration of 100 ng/ml.

| Reaction composition: | |
|---|---|
| Template DNA | 1 $\mu$L |
| Distilled water | 37.5 $\mu$L |
| dNTP | 4 $\mu$L |
| N-terminal primer | 1 $\mu$L |
| C-terminal primer | 1 $\mu$L |
| ×10 PCR buffer | 5 $\mu$L |
| Ex Taq | 0.5 $\mu$L |

| Reaction Steps | |
|---|---|
| Step 1 | 95° C. 5 min. |
| Step 2 | 95° C. 1 min. |
| Step 3 | 54° C. 1 min. |
| Step 4 | 72° C. 2 min. |
| Step 5 | 1 cycle of Steps 2 to 4 was repeated for 29 cycles. |
| Step 6 | 72° C. 8 min. |

The N-terminal primer has a Nde I site added and C-terminal primer has a BamH I site added. The amplified genes were digested with both restriction enzymes (Takara Shuzo Co., Ltd). Digestion was performed using 10 units of the restriction enzymes per $\mu$g of DNA at 37° C. for 2 hours. The special buffer attached to the restriction enzymes was used as the reaction composition according to the manufacturer's instructions. In the following examples, the same digestion conditions for restriction enzymes as described above were applied unless otherwise specified.

DNAs at both ends containing no V1 region were removed using MicroSpin Column S400 (Pharmacia).

(2) Construction of Circular DNA of Interest

Double digestion was performed on an expression vector pET3a using Nde I and BamH I. Then a main segment of the vector was purified using the above Micro Spin Column S400.

The pET3a digested with Nde I and BamH I was ligated to the above fragments amplified by PCR using DNA ligation kit (Takara Shuzo Co., Ltd) according to the instructions attached thereto, constructing the circular DNA of interest.

EXAMPLE 2

Transformation of *E.coli* with pDP5

Transformation was performed by introducing *E.coli* strain JM109 into the circular DNA obtained in Example 1, thereby obtaining a transformant. This transformation was conducted according to the $CaCl_2$ transformation method (see Hanahen D., J. Mol.Biol., 166:557–580 (1983)).

This transformant was cultured in LB medium containing 50 $\mu$g/mL ampicillin in an incubator overnight at 37° C. Cells were collected from the culture fluid by centrifugation at 10,000×g for 10 minutes at 4° C.

A plasmid was extracted and purified from the resulting cells according to alkaline SDS method (Birnboim, H. C. and Doly J., Nucleic Acid Research, 7:1513–1523(1979)). That is, the cells were suspended in glucose buffer and lysed in 1% SDS, 0.4 N NaOH solution. After neutralization with potassium acetate, the solution was centrifuged. Then the precipitates were collected, treated with phenol, and then added with ethanol, precipitating a plasmid.

The nucleotide sequence of the resulting plasmid pDP5 was tested by Sequenase kit (United States Biochemical Corporation, U.S.) according to a dideoxy method in order to confirm that the insert of interest has been inserted correctly and any unexpected changes have not occurred both before and after the insert. The term "change" includes such a change that the insert is shortened.

EXAMPLE 3

Construction of DiNCF V2 Expression Vector

A DiNCF V2 expression vector was constructed according to a method basically similar to that for constructing DiNCF V1. That is, the DiNCF V2 expression vector was constructed in the same manner as that of DiNCF V1 except that a C-terminal primer was different from that used in the steps for amplifying inserted genes in PCR. This C-terminal primer used herein was as follows:

5'-CTAAAGGATCCTATCACCGCTTACGCCTTTCATG TATCA-3' (SEQ ID NO:18)

The DiNCF V2 expression vector obtained using the above C-terminal primer was named pDP4.

The sequence was confirmed in the same manner as described above. The sequence of expression vectors constructed in the following examples was also confirmed in the same way.

EXAMPLE 4

Construction of Vectors for Expressing DiNCF V1+V1 (V1+V1) and DiNCF V2+V1 (V2+V1)

5 $\mu$g of pDP5, a vector for expressing DiNCF V1, was completely digested with 50 units of restriction enzyme Nsp V.

This digested fragments were treated with phenol according to the standard techniques, and then dephosphorylated using 20 units of bovine intestine alkaline phosphatase (CIP, SIGMA). After the treatment, phenol was used as a denaturant and the resultant products were separated into an aqueous layer containing the digested fragments and a phenol layer. Then the aqueous layer was sampled. This phenol treatment deactivated the enzymes.

On the other hand, 5 $\mu$g of pDi6, which was a vector containing DiNCF genes connected in tandem with each other in the order of V1, V2 and V1 regions, was digested with 20 units of a restriction enzyme Nsp V. The digested products were subjected to 2% agarose gel electrophoresis, thereby purifying about a 400 bp band using Gene Clean II Kit (Funakoshi Co., Ltd).

The above 400 bp fragment was ligated to the above linearized pDP5 treated with CIP. This ligation was performed in the same manner as described above. Using the ligated DNA, *E.coli* JM109 was transformed.

The several strains of resulting transformant clones were selected appropriately, and cultured in LB medium overnight at 37° C. in the presence of 50 μg/mL ampicillin. Cells were collected by centrifuging the culture solution at 10,000×g for 10 minutes at 4° C. Plasmid DNAs were extracted from the cells and purified by the alkaline SDS method (as described above).

Each obtained plasmid was digested with Nde I and BamH I and then analyzed by 1.5% agarose electrophoresis.

About an 800 bp band appeared as expected for a gene where V2 was bound to V1 or V2. A plasmid from the clone for which the 800 bp band has appeared was digested with 10 units of restriction enzyme AlwN I. The digested DNA was analyzed with 1.2% agarose gel electrophoresis.

This enzyme treatment resulted in the generation of three bands, 2.9 kbp, 2.1 kbp, and 0.4 kbp, respectively for V1+V1. For V2+V1, two bands of 3.3 kbp and 2.1 kbp were generated, respectively. The generation of these bands was considered as an analytical indicator so that two plasmids of interest were obtained.

The V1+V1 expression vector was named pDP18; the V2+V1 expression vector was named pDP17.

EXAMPLE 5

Construction of Vector for Expressing DiNCF V1+V2 (V1+V2) and DiNCF V2+V2 (V2+V2)

Vectors for expressing DiNCF V1+V2 and DiNCF V2+V2 were constructed in basically the same manner as in the method for producing the above vectors for DiNCF V1+V1 and DiNCF V2+V1. The difference was that in the first step pDP5 was digested with Nsp V in. Example 4, but in this example pDP4 was digested with Nsp V. Except this difference, vectors were constructed in the same way as in Example 4.

When the above vectors for expressing DiNCF V1+V2 and DiNCF V2+V2 were constructed, three bands of 2.9 kbp, 2.1 kbp and 0.4 kbp were observed for V1+V1 in electrophoresis and the two bands of 3.3 kbp and 2.1 kbp for V2+V1.

However, two bands with molecular weight of 2.9 kbp and 2.5 kbp, respectively were observed for the vector for expressing DiNCF V1+V2; one band for DiNCF V2+V2.

The appearance of these bands was considered as an indicator, thereby obtaining two plasmids. The V1+V2 expression vector was named pDP7, and the V2+V2 expression vector was named pDP9.

EXAMPLE 6

Construction of Vectors for Expressing DiNCF V1+V2+V1 (V1+V2+V1)

(1) Production of Fragment to be Inserted

Ten μg of pDi6 was partially digested with 8 units of a restriction enzyme Nsp V at 25° C. for 30 minutes.

This partially digested pDi6 was subjected to 1.5% agarose gel eletrophoresis and a fragment with a band of about 800 bp observed on the gel was purified using Gene Clean II Kt (Funakoshi Co., Ltd).

This purified 800 bp fragment was ligated to the pDP4, which had already been digested with Nsp V and treated with CIP as described in the method for constructing the above vectors for expressing DiNCF V1+V1 and DiNCF V2+V1, in the same manner as in Example 1 using Ligation Kit (Takara Shuzo Co., Ltd).

(2) Transformation and Recovery of Vector of Interest

Using the DNA obtained by ligation as described above, *E.coli* JM109 was transformed by the $CaCl_2$ transformation method. That is, DNA at a concentration of 10 ng/mL was added to 0.1 mL of commercially available JM109 competent cells, then the mixture was allowed to stand in water for 30 minutes. Next, the mixture was incubated for 45 seconds at 42° C., then allowed to stand on ice for 1 to 2 minutes. SOC medium (LIFE TECHNOLOGIES ORIENTAL, INC.) previously heated to 37° C. was added to the mixture to obtain 1 mL of the resultant mixture, then incubated for 1 hour at 37° C. Subsequently 100 μL of this solution was inoculated on LB agar medium, then allowed to stand overnight at 37° C., thereby obtaining transformant D050 strain.

Some of the transformant D050 strain were properly selected and cultured in LB medium (5 mL) containing 50 μg of ampicillin overnight at 37° C. This culture fluid was centrifuged at 10,000×g for 10 minutes at 4° C., then the cells were collected. The plasmid DNAs of interest were extracted from the cells and purified by the alkaline SDS method (Birnboim, H. C. and Doly J., Nucleic Acid Research, 7:1513–1523 (1979)).

Each of the obtained plasmids was digested with Nde I and BamH I, then analyzed by 1.5% agarose electrophoresis.

A plasmid containing V1+V2+V1 gene of interest leads to the generation of about a 1,200 bp band. Accordingly, plasmids derived from clones, for which a 1,200 band has appeared, were digested with 10 units of a restriction enzyme AlwN I for 2 hours at 37° C.

Subsequently, DNA digested as described above was analyzed by 1.2% agarose gel electrophoresis.

In the above method, a molecular weight differs depending on the direction for a fragment to be inserted. That is, a fragment is not always inserted into an expected direction, 5' to 3' but also into the opposite, 3' to 5' direction. For example, when AlwN I-digested fragment was inserted into the expected direction, three bands; 2.9 kbp, 2.1 kbp and 0.8 kbp, were observed. When the fragment was inserted into the opposite direction, three bands; 3.2 kbp, 2.1 kbp, and 0.3 kbp, were observed. Clones for which the three bands; 2.9 kbp, 2.1 kbp, and 0.8 kbp, were shown when the fragment was inserted into the expected direction, were selected. The clone was named pDP27.

EXAMPLE 7

Preparation of Various Expression Transformant

*E.coli* HMS174 (DE3) was transformed using seven vectors, pDP4, pDP5, pDP7, pDP9, pDP17, pDP18, and pDP27, constructed as in Examples 1 to 6. Transformation was performed by the methods in Examples above.

The transformants obtained by this transformation were named D025, D012, D027, D029, D037, D038, and D057, respectively.

EXAMPLE 8

Confirmation of Expression of Protein According to the Present Invention

Various transformants obtained in Example 7 have been cultured in 1,000 mL of M9ZB medium in $CO_2$ incubator at 37° C. until the absorbance $A_{550}$ became 0.8. The composition of M9ZB medium is as follows.

| | |
|---|---|
| NZ amine | 10 g |
| NaCl | 5 g |
| $NH_4Cl$ | 1 g |
| $KH_2PO_4$ | 3 g |
| $Na_2HPO_4$ | 6 g |

-continued

| | |
|---|---|
| Glucose | 10 g |
| Distilled water | 1 L |

NZ amine was purchased from WAKO Pure Chemical Industries., Ltd.

When the absorbance $A_{550}$ became 0.8, IPTG (isopropyltiogalactoside) was added to the medium so as to prepare the final concentration to 0.5 mM, followed by culture for 2.5 hours.

This culture medium was centrifuged at 10,000×g for 10 minutes at 4° C., then cells were collected. The cells from 1.5 mL of the culture fluid were suspended in a solution containing 0.1 mL of 8M urea and 0.1M Tris-HCl (pH 7.0). This suspension was subjected to ultrasonication using a sonicator, such as a Ultrasonic, centrifuged at 15,000 rpm (10,000×g) for 5 minutes at 4° C., obtaining the supernatant.

This supernatant was subjected to SDS polyacrylamide gel eletrophoresis using Phast System (Pharmacia) according to the manufacturer's instructions. As a control, *E.coli* strain transformed with a vector pET3a was used.

Comparison of the extract and control revealed the differences as described below. For the cell extract from the culture of D025 and D012 strains, a clear band with a molecular weight of about 14,000 was confined, while no band at the same position was confirmed for the control. In addition, a clear band of molecular weight of about 28,000 was confirmed for the cell extract from the culture of D027, C029, D037 and D038 strains, while at the same position no band was observed for the control. A clear band of molecular weight of about 43,000 was confirmed for the cell extract from the culture of D057 strain, while at the same position no band was observed for the control.

Therefore, it was confirmed by the manipulations above that the protein according to the present invention was produced.

EXAMPLE 9

Production and Purification of Protein of the Present Invention (1) Production of Protein of the Present Invention Various transformants obtained in Example 8 were cultured in a way similar to the method described above. IPTG was added similarly to induce expression.

(2) Extraction and Purification of Protein of the Present Invention Produced (2-1) Extraction of the Produced Protein of the Present Invention 1L of the culture fluid was centrifuged at 10,000×g for 10 minutes at 4° C. and then cells were collected. 20 ml of 50 mM hydrochloric acid was added to wet weight 10 g of the collected cells for suspension. Immediately after this step, the cell suspension was centrifuged at 16,000×g for 5 minutes at 4° C., removing the supernatant. Thereafter 100 mL of 100 mM hydrochloric acid was added to the remaining cells, and then allowed to stand for 15 minutes at 4° C. Subsequently, the mixture was centrifuged at 16,000×g for 5 minutes at 4° C., obtaining the supernatant (extract of hydrochloric acid).

(2-2) Purification of Protein of the Present Invention Produced

After the extract of hydrochloric acid was neutralized with 1N NaOH, ammonium sulfate was gradually added by dissolving into the solution to 60% saturation. When ammonium sulfate was completely dissolved, the mixture was allowed to stand for 2 hours at 4° C. Then the mixture was centrifuged at 16,000×g for 10 minutes at 4° C., obtaining the supernatant.

Ammonium sulfate was gradually added by dissolving into this supernatant to 90% saturation. When ammonium sulfate was dissolved completely, the mixture was allowed to stand for 2 hours at 4° C., then centrifuged at 16,000×g for 10 minutes at 4° C. After the supernatant was removed, the precipitate was dissolved in 5 mL of PBS (physiological phosphate buffer), then separated and purified by applying the mixture to Superdex 200 gel filtration chromatography (Pharmacia).

| Conditions for Chromatography | |
|---|---|
| Elution solvent: | PBS |
| Flow rate: | 0.5 ml/min |
| Detection | UV280 nm |
| Column: | 26 mm (diameter) × 600 mm |

Each component was separated in the condition above and each fraction detected by absorption was sampled. These fractions were analyzed by SDS polyacrylamide gel electrophoresis, so that fractions containing only the band of interest could be obtained as final purified products.

EXAMPLE 10

Elucidation of Physiological Effects of Protein of the Present Invention (1) Preparation of Lymphocytes 7 week old male BALB/c mice (3 mice per group) were sacrificed by dislocation of the cervical vertebra, and then the spleens were aseptically removed. The spleen was washed with sterilized PBS, ground down on frosted grass, suspended in PBS, filtrated with nylon mesh, and then such as the tissue fragments were removed.

The resultant filtrate was centrifuged at 500×g for 5 minutes at 4° C. The supernatant was removed to collect cells. The cells were resuspended in PBS. This step was repeated for three times to wash the cells.

1 mL of ACT solution cooled to 4° C. was added to the cells corresponding to one spleen and well stirred. Immediately after stirring, the mixture was cooled and centrifuged at 500×g for 5 minutes at 4° C., and then washed with PBS for three times. Washing was done in a way similar to the methods as described above. The washed cells corresponding to one spleen was suspended in RPMI 1640 medium (GIBCO) containing 1 mL of 5% fetal calf serum (FCS). Thus obtained cells were prepared as splenic lymphocyte solution.

(2) Preparation of B Cells

10 μL of anti-Thy-1.2 antibodies (Becton Dickinson Labware, U.S.A.) was added to the spleen lymphocyte solution obtained in (1) above, and then allowed to stand for 1 hour at 4° C. The mixture was washed once with PBS, and then suspended in RPMI 1640 medium containing 900 μL of 5% FCS. 100 μL of complement solution (rabbit antibody with low cytotoxicity, manufactured by Cedarlane Laboratories) was added to this suspension. The mixture was well stirred, then allowed to react for 1 hour at 37° C. The mixture was stirred every 15 minutes during reaction.

After the reaction was completed, the suspension was washed twice with PBS, suspended in RPMI1640 medium containing 5% FCS to a concentration of $8\times10^5$/mL, so that B cell suspension was obtained.

(3) Proliferative Response to Stimulation

B cell suspension prepared in (2) above, 500 μL per well, was added to 24-well plates, and cultured in RPMI1640 medium containing 5% FCS in the presence of 5% $CO_2$ at 37° C. One hour after the culture has started, the protein of this invention at a concentration of 1 to 10 μg/ml was added. After the addition of the protein, the suspension was cultured for 48 hours in the conditions described above. The extent of the cell growth was determined by MTT assay (Mosmann T., et al., J. Inmunol. Methods, 65:55–63, 1983).

That is, 50 μL of MTT solution having the following composition was added to 500 μL of cell suspension and allowed to stand for 4 hours at 37° C. Next, 450 μL stop solution having the composition as shown below, was added to the mixture in order to stop the reaction, then allowed to stand for 30 minutes at room temperature. Then the absorbance was determined at 630 nm and at 570 nm, each referred to as $A_{630}$ and $A_{570}$.

MTT solution: MTT (3-[4,5-Dimethylthiazol-2-yl]-2,5-diphenyltetrazolium bromide, Sigma) dissolved in PBS at a concentration of 5 mg/mL.

Stop solution: isopropanol containing 0.04N hydrochloric acid

In a blank experiment, the medium was treated in the same manner and the absorbance determined at 630 nm and at 570 nm, each referred to as $A0_{630}$ and $A0_{570}$, were used. MTT assay values were obtained by the following formula.

$$MTT \text{ assay value}=(A_{570}-A_{630})-(A0_{570}-A0_{630})$$

Table 2 shows the results of proliferative response of B cell due to the protein of this invention, which was determined by the method above. LPS was used as a positive control.

As a control, culture to which no protein of this invention was added was performed in (3) and MTT assay values were similarly determined.

TABLE 2

Results of MTT Assay

| Protein of This Invention | MTT Assay |
|---|---|
| V1 | 0.588 |
| V2 | 0.458 |
| V1 + V1 | 0.580 |
| V2 + V1 | 0.425 |
| V1 + V2 + V1 | 0.374 |
| Control | 0.276 |
| LPS | 0.556 |

From the results above, increased results of MTT assay, suggesting the presence of proliferative response of B cell to the protein of this invention, was confirmed. V1+V1 caused B cell proliferative response to stimulation almost equivalent to that by V1. For V2, V2+V1, and V1+V2+V1, proliferative response of B cell to stimulation was also confirmed.

EXAMPLE 11

Confirmation of Induced IgE Production (1) Induction of IgE Production

The mixture of 1 μg of DiNCF V1 and 200 μl of ALUM was administered intraperitoneally to 7 week old male BALB/c mice (3 mice per group).

Blood was collected with a heparinized tube from the caudal artery before the administration, and on the 7th, 14th and 21st days after the administration. The collected blood was centrifuged at 10,000×g for 5 minutes at 25° C. to separate the plasma.

IgE in the plasma was determined by the enzyme antibody technique. IgE was determined by the enzyme antibody technique as described below.

(2) IgE Determination Reagent

The following reagents were used as determination reagents. Anti-DNPIgE (YAMASA CORPORATION) was used as a standard IgE. Anti-mouse IgE Fc ε rat monoclonal antibody (COSMO BIO CO.,Ltd) was used as a primary antibody; peroxidase-labelled anti-mouse IgE polyclonal antibody as a secondary antibody. A Block A (Dainippon Pharmaceutical Co., Ltd) was used as a blocking agent. PBS containing 0.1% bovine serum albumin was used as reaction buffer. PBS containing 0.05% Tween20 was used as PBS-Tween.

(3) IgE Determination

The primary antibodies were prepared to have a concentration of 5 μg/ml using 50 mM sodium carbonate buffer (pH 9.5). The antibodies were introduced into each well of a 96-well microtiter plate so that they were bound to the surface of each well.

The 96-well microtiter plate was allowed to stand for 16 hours at 4° C. After the solution was removed, Block A diluted to 4-fold with distilled water was added, 300 μL per well, so as to block the plate. The plate was allowed to stand for 1 hour at 37° C., and then washed three times with PBS-Tween.

100 μL each of the protein of the present invention or the standard IgE was added to each well, and it was allowed to react for 3 hours at 25° C. The plate was washed three times with PBS-Tween. 100 μL each of the secondary antibodies diluted to 10,000-fold with the reaction buffer was added to each well, allowed to react for 3 hours at 25° C., then washed three times with PBS-Tween.

100 μL each of substrate solution was introduced into each well, then allowed to stand for several minutes in the dark at room temperature. When the color was developed appropriately, 100 μL each of stop solution was added to each well. Using a plate reader, the color at 490 nm was detected. IgE concentration in the plasma was calculated from the calibration curve obtained with the standard IgE.

Figure 6:
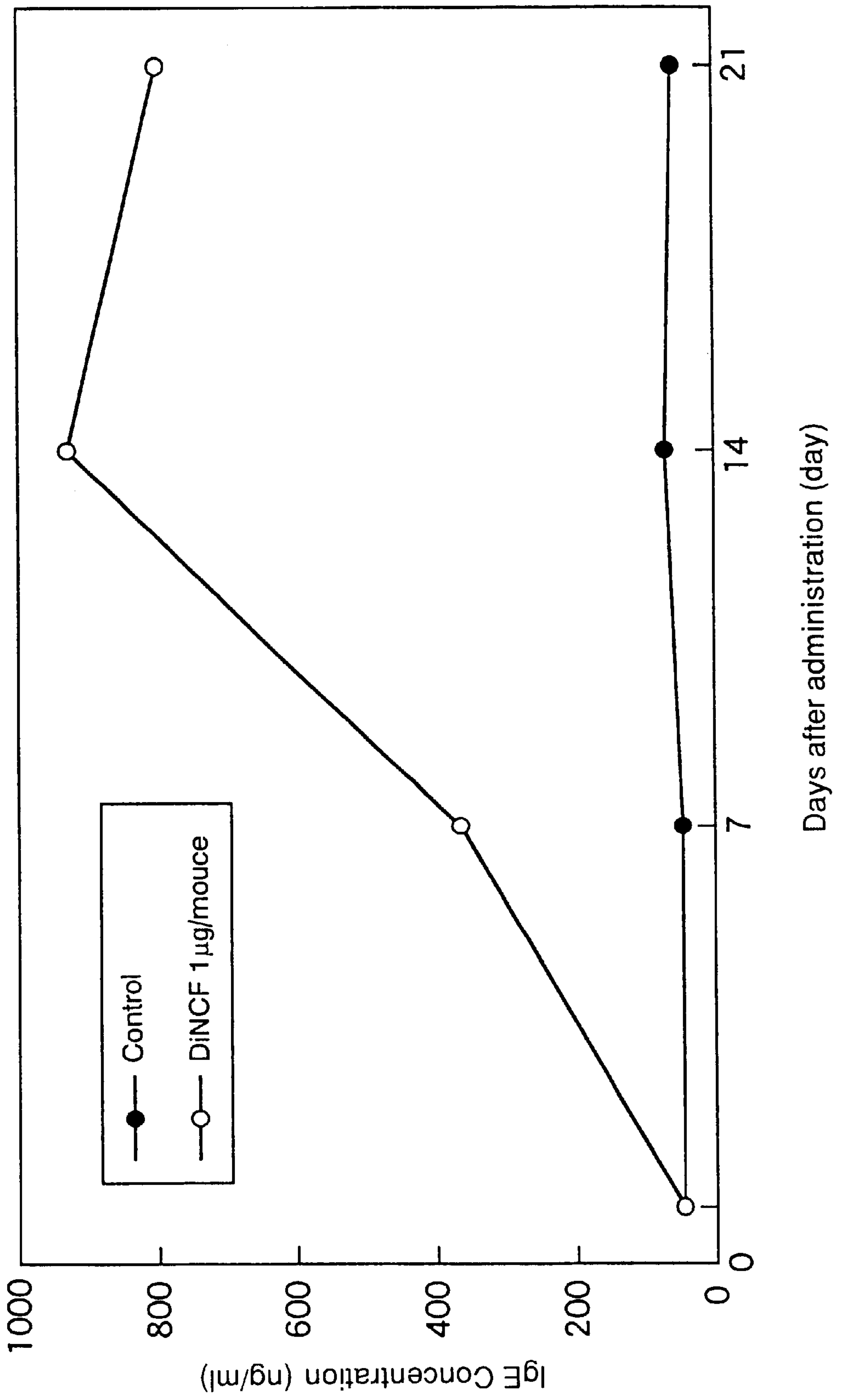
FIG. 6 shows changes in IgE level in the blood when V1 was administered.

FIG. 6 shows IgE concentration in the plasma prepared as described above.

EXAMPLE 12

Assessment of Protein of The Present Invention Based on Autoimmune Encephalomyelitis Model Female Lewis rats were divided into two groups, each consisting of 3 rats. 100 μg of DiNCF was administered to each rat of a V1-administered group, via the foot pads of the hind legs. Similarly, PBS was administered to a control group. This administration continued for 41 days. On the 41st day after the administration has started, both test and control groups were further administrated with guinea pig myelin basic protein peptide (GPE) emulsified with complete Freund's adjuvant, in an amount of 5 μg per rat.

On the 14th day after the GPE administration, changes in clinical signs of both groups were scored for assessment. The scores were evaluated based on the criteria as shown in Table 1.

Results of assessment as described above were shown in Table 3 below.

TABLE 3

Assessment of Protein of the Present Invention based on Autoimmune Encephalomyelitis Model

| Group | Amount of DiNCF V1 administered (μg/animal) First (d-41) | Second (d0) | Amount of GPE administered for immunization (μg) | Incidence Rate (%) | Clinical Score |
|---|---|---|---|---|---|
| DiNCF V1 | 100 | 100 | 5 | 33 (1/3) | 0.7 (2,0,0) |
| Control | 0 | 0 | 5 | 100 (3/3) | 2.7 (3,2,2) |

d-41 denotes on the 41st day before immunization with GPE.
d0 denotes a day on which GPE was administered for immunization.

While the control group demonstrated the incidence rate of 100% and the clinical score of 2.7, DiNCF-administered group demonstrated the incidence rate of 33% and the clinical score of 0.7. It was suggested that DiNCF V1 significantly inhibited the incidence of autoimmune encephalomyelitis.

EXAMPLE 13

Assessment of Protein of the Present Invention Based on Suppression of Type-I Allergy (1) Administration of Agent 6 week old male Wister rats that have been quarantined for 7 days after delivery, acclimatized, and then anesthetized with ether. The rat body hairs of its dorsum part were cut, the skin was incised along the body, and then an about 30 mm long, subcutaneous pocket was made using tweezers. 200 μl of 1 mg/ml DiNCF V1 dissolved in physiological phosphoric acid buffer was introduced into an osmotic pump (type 2002, ALZA Corporation). Then the pump was inserted into the pocket. Only a physiological phosphate buffer was used for a control group. The incised part was sutured after the insertion.

(2) Induction of Passive Anaphylaxis

On the 21st day after the administration of agent, rats were anesthetized with ether, and then the hairs of the body front were cut. Anti-DNP-Ascaris antibodies (LSL, titer 256:1) diluted to 400-fold with physiological saline were injected subcutaneously to 10 sites (0.1 ml per 5 sites).

48 hours after the injection with the antibodies, 1 ml of 0.5% Evance Blue physiological saline solution containing 1 mg of DNP-Ascaris antigens was injected into the caudal vein.

30 minutes later, the rats were sacrificed by dislocation of the cervical vertebra, and then skin on the dorsum was separated. Leakage of blue pigments at the site administered with antibodies was photographed from the back side of the skin.

(3) Assessment

The pigment density at the photographed site where pigments have leaked was measured with a densitometer (Atto Corporation) and compared to the control group.

(4) Results

Figure 7:
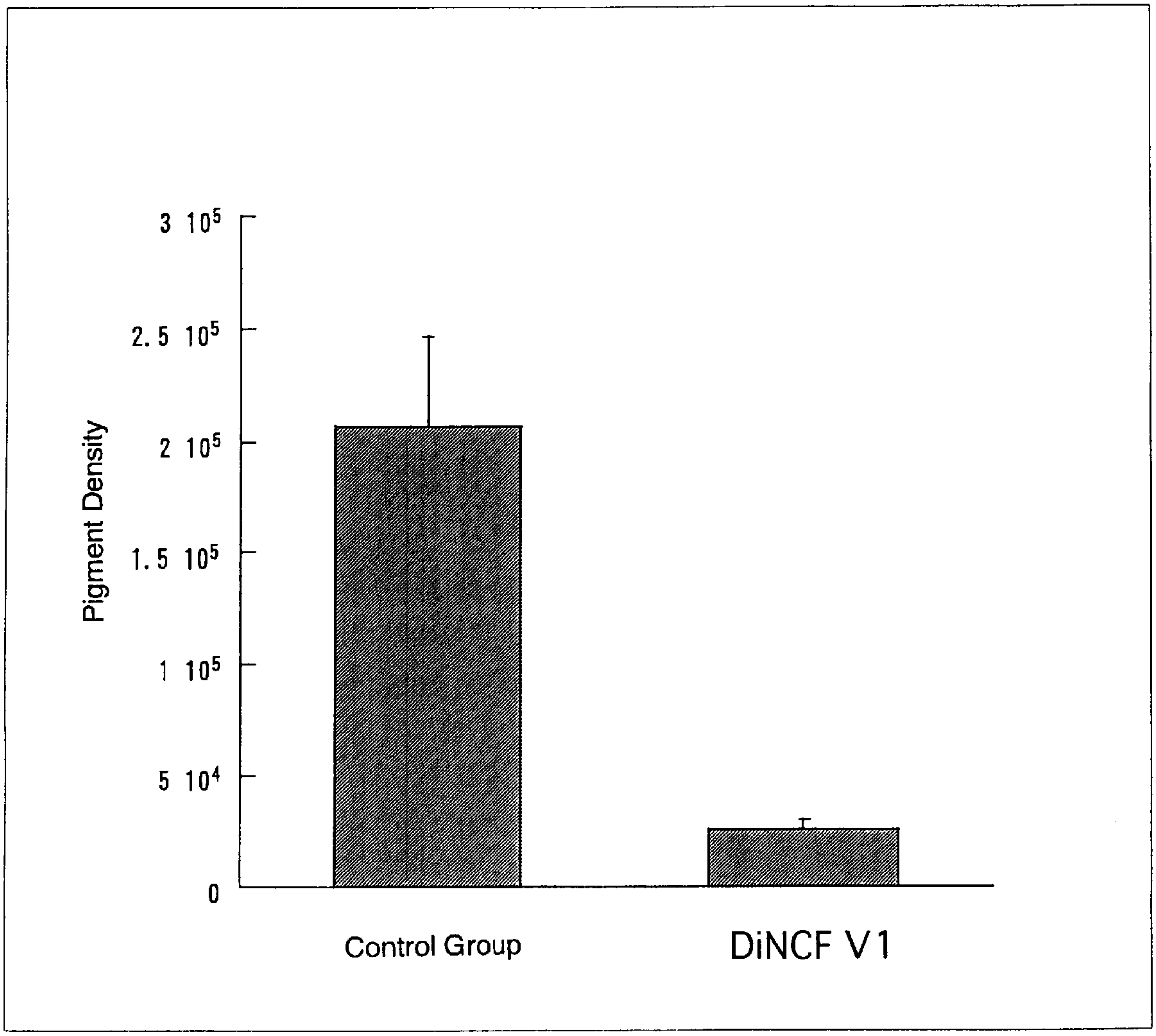
FIG. 7 shows suppression of passive anaphylaxis reaction in a rat to which the protein according to the present invention was administered.

Results as evaluated by the method described above were shown in FIG. 7. These results were calculated from the mean value for three rats per group. Therefore, it was shown that in DiNCF-administered group, leakage of blue pigments caused by passive anaphylaxis reaction was significantly inhibited in comparison to the control group. Thus DiNCF was shown to have effect on Type-I allergosis, such as atopic dermatits, chronic bronchitis, and pollinosis.

All publications, patents and patent applications cited herein are incorporated herein by reference in their entirety.

Industrail Applicability

The present invention provides proteins having immunomodulatory activity. Further the invention provides proteins capable of stimulating IgE production. These proteins are useful as immunomodulating agents. That is, these proteins of this invention can be applied to treatment of various diseases related to abnormalities in the immune system when they are prepared as immunomodulating agents or as IgE production-stimulating agents by mixing with components normally used in other pharmaceutical compositions, such as excipient or the like.

What is claimed is:

1. An immunomodulatory method for treating autoimmune encephalomyelitis, comprising:

administering to a patient in need of such treatment, an effective amount of a protein comprising an amino acid sequence of SEQ ID NO: 1.

* * * * *

SEQUENCE LISTING

```
<160> NUMBER OF SEQ ID NOS: 18

<210> SEQ ID NO 1
<211> LENGTH: 129
<212> TYPE: PRT
<213> ORGANISM: Artificial Sequence
<220> FEATURE:
<223> OTHER INFORMATION: Synthetic protein

<400> SEQUENCE: 1

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
             20                  25                  30

Ser Lys Met Asp Ile Gln Lys Lys Ile Phe Asp Tyr Phe Glu Ser Leu
         35                  40                  45

Thr Gly Asp Lys Lys Lys Lys Ala Ala Glu Glu Leu Gln Gln Gly Cys
     50                  55                  60

Leu Met Ala Leu Ser Glu Ile Ile Gly Asn Glu Lys Met Leu Met Leu
 65                  70                  75                  80

Lys Glu Ile Lys Asp Ser Gly Ala Asp Pro Glu Gln Ile Glu Asp Met
```

-continued

```
                 85                  90                  95

Leu Lys Leu Val Val Asp Lys Glu Lys Lys Lys Arg Ile Asp Glu Tyr
            100                 105                 110

Pro Pro Val Cys Arg Lys Ile Tyr Ala Ala Met Asn Glu Arg Arg Lys
        115                 120                 125

Arg


<210> SEQ ID NO 2
<211> LENGTH: 131
<212> TYPE: PRT
<213> ORGANISM: Artificial Sequence
<220> FEATURE:
<223> OTHER INFORMATION: Synthetic protein

<400> SEQUENCE: 2

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
             20                  25                  30

Ser Lys Met Asp Ile Gln Lys Lys Ile Phe Asp Tyr Phe Glu Ser Leu
         35                  40                  45

Thr Gly Asp Lys Lys Lys Lys Ala Ala Glu Glu Leu Gln Gly Cys Arg
     50                  55                  60

Met Ala Leu Arg Glu Ile Val Gly Glu Glu Lys Trp Thr Val Leu Arg
 65                  70                  75                  80

Gln Met Lys Asp Ser Ala Thr Pro Lys Glu Leu Ser Met Lys Val Glu
                 85                  90                  95

Glu Met Phe Lys Asp Val Ile Asp Lys Asp Lys Lys Glu Lys Ile Asp
            100                 105                 110

Glu Tyr Ala Pro Val Cys Arg Lys Ile Phe Ala Val Ile His Glu Arg
        115                 120                 125

Arg Lys Arg
    130


<210> SEQ ID NO 3
<211> LENGTH: 260
<212> TYPE: PRT
<213> ORGANISM: Artificial Sequence
<220> FEATURE:
<223> OTHER INFORMATION: Synthetic protein

<400> SEQUENCE: 3

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
             20                  25                  30

Ser Lys Met Asp Ile Gln Lys Lys Ile Phe Asp Tyr Phe Glu Ser Leu
         35                  40                  45

Thr Gly Asp Lys Lys Lys Lys Ala Ala Glu Glu Leu Gln Gln Gly Cys
     50                  55                  60

Leu Met Ala Leu Ser Glu Ile Ile Gly Asn Glu Lys Met Leu Met Leu
 65                  70                  75                  80

Lys Glu Ile Lys Asp Ser Gly Ala Asp Pro Glu Gln Ile Glu Asp Met
                 85                  90                  95

Leu Lys Leu Val Val Asp Lys Glu Lys Lys Lys Arg Ile Asp Glu Tyr
            100                 105                 110

Pro Pro Val Cys Arg Lys Ile Tyr Ala Ala Met Asn Glu Arg Arg Lys
```

-continued

```
        115                 120                 125

Arg Asn Asp His Asn Leu Glu Ser Tyr Phe Gln Thr Tyr Leu Ser Trp
    130                 135                 140

Leu Thr Asp Ala Gln Lys Asp Glu Ile Lys Lys Met Lys Glu Glu Gly
145                 150                 155                 160

Lys Ser Lys Met Asp Ile Gln Lys Lys Ile Phe Asp Tyr Phe Glu Ser
                165                 170                 175

Leu Thr Gly Asp Lys Lys Lys Lys Ala Ala Glu Glu Leu Gln Gly Cys
            180                 185                 190

Arg Met Ala Leu Arg Glu Ile Val Gly Glu Glu Lys Trp Thr Val Leu
        195                 200                 205

Arg Gln Met Lys Asp Ser Ala Thr Pro Lys Glu Leu Ser Met Lys Val
    210                 215                 220

Glu Glu Met Phe Lys Asp Val Ile Asp Lys Asp Lys Lys Glu Lys Ile
225                 230                 235                 240

Asp Glu Tyr Ala Pro Val Cys Arg Lys Ile Phe Ala Val Ile His Glu
                245                 250                 255

Arg Arg Lys Arg
            260


<210> SEQ ID NO 4
<211> LENGTH: 260
<212> TYPE: PRT
<213> ORGANISM: Artificial Sequence
<220> FEATURE:
<223> OTHER INFORMATION: Synthetic protein

<400> SEQUENCE: 4

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
            20                  25                  30

Ser Lys Met Asp Ile Gln Lys Lys Ile Phe Asp Tyr Phe Glu Ser Leu
        35                  40                  45

Thr Gly Asp Lys Lys Lys Lys Ala Ala Glu Glu Leu Gln Gly Cys Arg
     50                  55                  60

Met Ala Leu Arg Glu Ile Val Gly Glu Glu Lys Trp Thr Val Leu Arg
 65                  70                  75                  80

Gln Met Lys Asp Ser Ala Thr Pro Lys Glu Leu Ser Met Lys Val Glu
                85                  90                  95

Glu Met Phe Lys Asp Val Ile Asp Lys Asp Lys Lys Glu Lys Ile Asp
            100                 105                 110

Glu Tyr Ala Pro Val Cys Arg Lys Ile Phe Ala Val Ile His Glu Arg
        115                 120                 125

Arg Lys Arg Asn Asp His Asn Leu Glu Ser Tyr Phe Gln Thr Tyr Leu
    130                 135                 140

Ser Trp Leu Thr Asp Ala Gln Lys Asp Glu Ile Lys Lys Met Lys Glu
145                 150                 155                 160

Glu Gly Lys Ser Lys Met Asp Ile Gln Lys Lys Ile Phe Asp Tyr Phe
                165                 170                 175

Glu Ser Leu Thr Gly Asp Lys Lys Lys Lys Ala Ala Glu Glu Leu Gln
            180                 185                 190

Gln Gly Cys Leu Met Ala Leu Ser Glu Ile Ile Gly Asn Glu Lys Met
        195                 200                 205

Leu Met Leu Lys Glu Ile Lys Asp Ser Gly Ala Asp Pro Glu Gln Ile
```

-continued

```
    210                 215                 220

Glu Asp Met Leu Lys Leu Val Val Asp Lys Glu Lys Lys Lys Arg Ile
225                 230                 235                 240

Asp Glu Tyr Pro Pro Val Cys Arg Lys Ile Tyr Ala Ala Met Asn Glu
                245                 250                 255

Arg Arg Lys Arg
            260


<210> SEQ ID NO 5
<211> LENGTH: 389
<212> TYPE: PRT
<213> ORGANISM: Artificial Sequence
<220> FEATURE:
<223> OTHER INFORMATION: Synthetic protein

<400> SEQUENCE: 5

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
            20                  25                  30

Ser Lys Met Asp Ile Gln Lys Lys Ile Phe Asp Tyr Phe Glu Ser Leu
        35                  40                  45

Thr Gly Asp Lys Lys Lys Lys Ala Ala Glu Glu Leu Gln Gln Gly Cys
     50                  55                  60

Leu Met Ala Leu Ser Glu Ile Ile Gly Asn Glu Lys Met Leu Met Leu
 65                  70                  75                  80

Lys Glu Ile Lys Asp Ser Gly Ala Asp Pro Glu Gln Ile Glu Asp Met
                 85                  90                  95

Leu Lys Leu Val Val Asp Lys Glu Lys Lys Lys Arg Ile Asp Glu Tyr
            100                 105                 110

Pro Pro Val Cys Arg Lys Ile Tyr Ala Ala Met Asn Glu Arg Arg Lys
        115                 120                 125

Arg Asn Asp His Asn Leu Glu Ser Tyr Phe Gln Thr Tyr Leu Ser Trp
    130                 135                 140

Leu Thr Asp Ala Gln Lys Asp Glu Ile Lys Lys Met Lys Glu Glu Gly
145                 150                 155                 160

Lys Ser Lys Met Asp Ile Gln Lys Lys Ile Phe Asp Tyr Phe Glu Ser
                165                 170                 175

Leu Thr Gly Asp Lys Lys Lys Lys Ala Ala Glu Glu Leu Gln Gly Cys
            180                 185                 190

Arg Met Ala Leu Arg Glu Ile Val Gly Glu Glu Lys Trp Thr Val Leu
        195                 200                 205

Arg Gln Met Lys Asp Ser Ala Thr Pro Lys Glu Leu Ser Met Lys Val
    210                 215                 220

Glu Glu Met Phe Lys Asp Val Ile Asp Lys Asp Lys Lys Glu Lys Ile
225                 230                 235                 240

Asp Glu Tyr Ala Pro Val Cys Arg Lys Ile Phe Ala Val Ile His Glu
                245                 250                 255

Arg Arg Lys Arg Asn Asp His Asn Leu Glu Ser Tyr Phe Gln Thr Tyr
            260                 265                 270

Leu Ser Trp Leu Thr Asp Ala Gln Lys Asp Glu Ile Lys Lys Met Lys
        275                 280                 285

Glu Glu Gly Lys Ser Lys Met Asp Ile Gln Lys Lys Ile Phe Asp Tyr
    290                 295                 300

Phe Glu Ser Leu Thr Gly Asp Lys Lys Lys Lys Ala Ala Glu Glu Leu
```

-continued 305 310 315 320

Gln Gln Gly Cys Leu Met Ala Leu Ser Glu Ile Ile Gly Asn Glu Lys
325 330 335

Met Leu Met Leu Lys Glu Ile Lys Asp Ser Gly Ala Asp Pro Glu Gln
340 345 350

Ile Glu Asp Met Leu Lys Leu Val Val Asp Lys Glu Lys Lys Lys Arg
355 360 365

Ile Asp Glu Tyr Pro Pro Val Cys Arg Lys Ile Tyr Ala Ala Met Asn
370 375 380

Glu Arg Arg Lys Arg
385

<210> SEQ ID NO 6
<211> LENGTH: 391
<212> TYPE: PRT
<213> ORGANISM: Artificial Sequence
<220> FEATURE:
<223> OTHER INFORMATION: Synthetic protein

<400> SEQUENCE: 6

Asn Asp His Asn Leu Glu Ser Tyr Phe Gln Thr Tyr Leu Ser Trp Leu
1 5 10 15

Thr Asp Ala Gln Lys Asp Glu Ile Lys Lys Met Lys Glu Glu Gly Lys
20 25 30

Ser Lys Met Asp Ile Gln Lys Lys Ile Phe Asp Tyr Phe Glu Ser Leu
35 40 45

Thr Gly Asp Lys Lys Lys Lys Ala Ala Glu Glu Leu Gln Gly Cys Arg
50 55 60

Met Ala Leu Arg Glu Ile Val Gly Glu Glu Lys Trp Thr Val Leu Arg
65 70 75 80

Gln Met Lys Asp Ser Ala Thr Pro Lys Glu Leu Ser Met Lys Val Glu
85 90 95

Glu Met Phe Lys Asp Val Ile Asp Lys Asp Lys Lys Glu Lys Ile Asp
100 105 110

Glu Tyr Ala Pro Val Cys Arg Lys Ile Phe Ala Val Ile His Glu Arg
115 120 125

Arg Lys Arg Asn Asp His Asn Leu Glu Ser Tyr Phe Gln Thr Tyr Leu
130 135 140

Ser Trp Leu Thr Asp Ala Gln Lys Asp Glu Ile Lys Lys Met Lys Glu
145 150 155 160

Glu Gly Lys Ser Lys Met Asp Ile Gln Lys Lys Ile Phe Asp Tyr Phe
165 170 175

Glu Ser Leu Thr Gly Asp Lys Lys Lys Lys Ala Ala Glu Glu Leu Gln
180 185 190

Gln Gly Cys Leu Met Ala Leu Ser Glu Ile Ile Gly Asn Glu Lys Met
195 200 205

Leu Met Leu Lys Glu Ile Lys Asp Ser Gly Ala Asp Pro Glu Gln Ile
210 215 220

Glu Asp Met Leu Lys Leu Val Val Asp Lys Glu Lys Lys Lys Arg Ile
225 230 235 240

Asp Glu Tyr Pro Pro Val Cys Arg Lys Ile Tyr Ala Ala Met Asn Glu
245 250 255

Arg Arg Lys Arg Asn Asp His Asn Leu Glu Ser Tyr Phe Gln Thr Tyr
260 265 270

Leu Ser Trp Leu Thr Asp Ala Gln Lys Asp Glu Ile Lys Lys Met Lys

-continued

```
        275                 280                 285

Glu Glu Gly Lys Ser Lys Met Asp Ile Gln Lys Lys Ile Phe Asp Tyr
    290                 295                 300

Phe Glu Ser Leu Thr Gly Asp Lys Lys Lys Lys Ala Ala Glu Glu Leu
305                 310                 315                 320

Gln Gly Cys Arg Met Ala Leu Arg Glu Ile Val Gly Glu Glu Lys Trp
                325                 330                 335

Thr Val Leu Arg Gln Met Lys Asp Ser Ala Thr Pro Lys Glu Leu Ser
            340                 345                 350

Met Lys Val Glu Glu Met Phe Lys Asp Val Ile Asp Lys Asp Lys Lys
        355                 360                 365

Glu Lys Ile Asp Glu Tyr Ala Pro Val Cys Arg Lys Ile Phe Ala Val
    370                 375                 380

Ile His Glu Arg Arg Lys Arg
385                 390


<210> SEQ ID NO 7
<211> LENGTH: 258
<212> TYPE: PRT
<213> ORGANISM: Artificial Sequence
<220> FEATURE:
<223> OTHER INFORMATION: Synthetic protein

<400> SEQUENCE: 7

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
            20                  25                  30

Ser Lys Met Asp Ile Gln Lys Lys Ile Phe Asp Tyr Phe Glu Ser Leu
        35                  40                  45

Thr Gly Asp Lys Lys Lys Lys Ala Ala Glu Glu Leu Gln Gln Gly Cys
     50                  55                  60

Leu Met Ala Leu Ser Glu Ile Ile Gly Asn Glu Lys Met Leu Met Leu
 65                  70                  75                  80

Lys Glu Ile Lys Asp Ser Gly Ala Asp Pro Glu Gln Ile Glu Asp Met
                 85                  90                  95

Leu Lys Leu Val Val Asp Lys Glu Lys Lys Arg Ile Asp Glu Tyr
            100                 105                 110

Pro Pro Val Cys Arg Lys Ile Tyr Ala Ala Met Asn Glu Arg Arg Lys
        115                 120                 125

Arg Asn Asp His Asn Leu Glu Ser Tyr Phe Gln Thr Tyr Leu Ser Trp
    130                 135                 140

Leu Thr Asp Ala Gln Lys Asp Glu Ile Lys Lys Met Lys Glu Glu Gly
145                 150                 155                 160

Lys Ser Lys Met Asp Ile Gln Lys Lys Ile Phe Asp Tyr Phe Glu Ser
                165                 170                 175

Leu Thr Gly Asp Lys Lys Lys Lys Ala Ala Glu Glu Leu Gln Gln Gly
            180                 185                 190

Cys Leu Met Ala Leu Ser Glu Ile Ile Gly Asn Glu Lys Met Leu Met
        195                 200                 205

Leu Lys Glu Ile Lys Asp Ser Gly Ala Asp Pro Glu Gln Ile Glu Asp
    210                 215                 220

Met Leu Lys Leu Val Val Asp Lys Glu Lys Lys Lys Arg Ile Asp Glu
225                 230                 235                 240

Tyr Pro Pro Val Cys Arg Lys Ile Tyr Ala Ala Met Asn Glu Arg Arg
```

-continued

```
            245                 250                 255

Lys Arg


<210> SEQ ID NO 8
<211> LENGTH: 262
<212> TYPE: PRT
<213> ORGANISM: Artificial Sequence
<220> FEATURE:
<223> OTHER INFORMATION: Synthetic protein

<400> SEQUENCE: 8

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
             20                  25                  30

Ser Lys Met Asp Ile Gln Lys Lys Ile Phe Asp Tyr Phe Glu Ser Leu
         35                  40                  45

Thr Gly Asp Lys Lys Lys Lys Ala Ala Glu Glu Leu Gln Gly Cys Arg
     50                  55                  60

Met Ala Leu Arg Glu Ile Val Gly Glu Glu Lys Trp Thr Val Leu Arg
 65                  70                  75                  80

Gln Met Lys Asp Ser Ala Thr Pro Lys Glu Leu Ser Met Lys Val Glu
                 85                  90                  95

Glu Met Phe Lys Asp Val Ile Asp Lys Asp Lys Lys Glu Lys Ile Asp
            100                 105                 110

Glu Tyr Ala Pro Val Cys Arg Lys Ile Phe Ala Val Ile His Glu Arg
        115                 120                 125

Arg Lys Arg Asn Asp His Asn Leu Glu Ser Tyr Phe Gln Thr Tyr Leu
    130                 135                 140

Ser Trp Leu Thr Asp Ala Gln Lys Asp Glu Ile Lys Lys Met Lys Glu
145                 150                 155                 160

Glu Gly Lys Ser Lys Met Asp Ile Gln Lys Lys Ile Phe Asp Tyr Phe
                165                 170                 175

Glu Ser Leu Thr Gly Asp Lys Lys Lys Lys Ala Ala Glu Glu Leu Gln
            180                 185                 190

Gly Cys Arg Met Ala Leu Arg Glu Ile Val Gly Glu Glu Lys Trp Thr
        195                 200                 205

Val Leu Arg Gln Met Lys Asp Ser Ala Thr Pro Lys Glu Leu Ser Met
    210                 215                 220

Lys Val Glu Glu Met Phe Lys Asp Val Ile Asp Lys Asp Lys Lys Glu
225                 230                 235                 240

Lys Ile Asp Glu Tyr Ala Pro Val Cys Arg Lys Ile Phe Ala Val Ile
                245                 250                 255

His Glu Arg Arg Lys Arg
            260


<210> SEQ ID NO 9
<211> LENGTH: 387
<212> TYPE: PRT
<213> ORGANISM: Artificial Sequence
<220> FEATURE:
<223> OTHER INFORMATION: Synthetic protein

<400> SEQUENCE: 9

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
```

-continued

```
            20                  25                  30

Ser Lys Met Asp Ile Gln Lys Lys Ile Phe Asp Tyr Phe Glu Ser Leu
        35                  40                  45

Thr Gly Asp Lys Lys Lys Lys Ala Ala Glu Glu Leu Gln Gln Gly Cys
    50                  55                  60

Leu Met Ala Leu Ser Glu Ile Ile Gly Asn Glu Lys Met Leu Met Leu
65                  70                  75                  80

Lys Glu Ile Lys Asp Ser Gly Ala Asp Pro Glu Gln Ile Glu Asp Met
                85                  90                  95

Leu Lys Leu Val Val Asp Lys Glu Lys Lys Arg Ile Asp Glu Tyr
            100                 105                 110

Pro Pro Val Cys Arg Lys Ile Tyr Ala Ala Met Asn Glu Arg Arg Lys
        115                 120                 125

Arg Asn Asp His Asn Leu Glu Ser Tyr Phe Gln Thr Tyr Leu Ser Trp
    130                 135                 140

Leu Thr Asp Ala Gln Lys Asp Glu Ile Lys Lys Met Lys Glu Glu Gly
145                 150                 155                 160

Lys Ser Lys Met Asp Ile Gln Lys Lys Ile Phe Asp Tyr Phe Glu Ser
                165                 170                 175

Leu Thr Gly Asp Lys Lys Lys Lys Ala Ala Glu Glu Leu Gln Gln Gly
            180                 185                 190

Cys Leu Met Ala Leu Ser Glu Ile Ile Gly Asn Glu Lys Met Leu Met
        195                 200                 205

Leu Lys Glu Ile Lys Asp Ser Gly Ala Asp Pro Glu Gln Ile Glu Asp
    210                 215                 220

Met Leu Lys Leu Val Val Asp Lys Glu Lys Lys Lys Arg Ile Asp Glu
225                 230                 235                 240

Tyr Pro Pro Val Cys Arg Lys Ile Tyr Ala Ala Met Asn Glu Arg Arg
                245                 250                 255

Lys Arg Asn Asp His Asn Leu Glu Ser Tyr Phe Gln Thr Tyr Leu Ser
            260                 265                 270

Trp Leu Thr Asp Ala Gln Lys Asp Glu Ile Lys Lys Met Lys Glu Glu
        275                 280                 285

Gly Lys Ser Lys Met Asp Ile Gln Lys Lys Ile Phe Asp Tyr Phe Glu
    290                 295                 300

Ser Leu Thr Gly Asp Lys Lys Lys Lys Ala Ala Glu Glu Leu Gln Gln
305                 310                 315                 320

Gly Cys Leu Met Ala Leu Ser Glu Ile Ile Gly Asn Glu Lys Met Leu
                325                 330                 335

Met Leu Lys Glu Ile Lys Asp Ser Gly Ala Asp Pro Glu Gln Ile Glu
            340                 345                 350

Asp Met Leu Lys Leu Val Val Asp Lys Glu Lys Lys Lys Arg Ile Asp
        355                 360                 365

Glu Tyr Pro Pro Val Cys Arg Lys Ile Tyr Ala Ala Met Asn Glu Arg
    370                 375                 380

Arg Lys Arg
385

<210> SEQ ID NO 10
<211> LENGTH: 389
<212> TYPE: PRT
<213> ORGANISM: Artificial Sequence
<220> FEATURE:
<223> OTHER INFORMATION: Synthetic protein
```

-continued

<400> SEQUENCE: 10

```
Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
             20                  25                  30

Ser Lys Met Asp Ile Gln Lys Lys Ile Phe Asp Tyr Phe Glu Ser Leu
         35                  40                  45

Thr Gly Asp Lys Lys Lys Lys Ala Ala Glu Glu Leu Gln Gln Gly Cys
     50                  55                  60

Leu Met Ala Leu Ser Glu Ile Ile Gly Asn Glu Lys Met Leu Met Leu
 65                  70                  75                  80

Lys Glu Ile Lys Asp Ser Gly Ala Asp Pro Glu Gln Ile Glu Asp Met
                 85                  90                  95

Leu Lys Leu Val Val Asp Lys Glu Lys Lys Lys Arg Ile Asp Glu Tyr
            100                 105                 110

Pro Pro Val Cys Arg Lys Ile Tyr Ala Ala Met Asn Glu Arg Arg Lys
        115                 120                 125

Arg Asn Asp His Asn Leu Glu Ser Tyr Phe Gln Thr Tyr Leu Ser Trp
    130                 135                 140

Leu Thr Asp Ala Gln Lys Asp Glu Ile Lys Lys Met Lys Glu Glu Gly
145                 150                 155                 160

Lys Ser Lys Met Asp Ile Gln Lys Lys Ile Phe Asp Tyr Phe Glu Ser
                165                 170                 175

Leu Thr Gly Asp Lys Lys Lys Lys Ala Ala Glu Glu Leu Gln Gln Gly
            180                 185                 190

Cys Leu Met Ala Leu Ser Glu Ile Ile Gly Asn Glu Lys Met Leu Met
        195                 200                 205

Leu Lys Glu Ile Lys Asp Ser Gly Ala Asp Pro Glu Gln Ile Glu Asp
    210                 215                 220

Met Leu Lys Leu Val Val Asp Lys Glu Lys Lys Lys Arg Ile Asp Glu
225                 230                 235                 240

Tyr Pro Pro Val Cys Arg Lys Ile Tyr Ala Ala Met Asn Glu Arg Arg
                245                 250                 255

Lys Arg Asn Asp His Asn Leu Glu Ser Tyr Phe Gln Thr Tyr Leu Ser
            260                 265                 270

Trp Leu Thr Asp Ala Gln Lys Asp Glu Ile Lys Lys Met Lys Glu Glu
        275                 280                 285

Gly Lys Ser Lys Met Asp Ile Gln Lys Lys Ile Phe Asp Tyr Phe Glu
    290                 295                 300

Ser Leu Thr Gly Asp Lys Lys Lys Lys Ala Ala Glu Glu Leu Gln Gly
305                 310                 315                 320

Cys Arg Met Ala Leu Arg Glu Ile Val Gly Glu Glu Lys Trp Thr Val
                325                 330                 335

Leu Arg Gln Met Lys Asp Ser Ala Thr Pro Lys Glu Leu Ser Met Lys
            340                 345                 350

Val Glu Glu Met Phe Lys Asp Val Ile Asp Lys Asp Lys Lys Glu Lys
        355                 360                 365

Ile Asp Glu Tyr Ala Pro Val Cys Arg Lys Ile Phe Ala Val Ile His
    370                 375                 380

Glu Arg Arg Lys Arg
385
```

<210> SEQ ID NO 11

-continued

```
<211> LENGTH: 391
<212> TYPE: PRT
<213> ORGANISM: Artificial Sequence
<220> FEATURE:
<223> OTHER INFORMATION: Synthetic protein

<400> SEQUENCE: 11

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
             20                  25                  30

Ser Lys Met Asp Ile Gln Lys Lys Ile Phe Asp Tyr Phe Glu Ser Leu
         35                  40                  45

Thr Gly Asp Lys Lys Lys Lys Ala Ala Glu Glu Leu Gln Gln Gly Cys
     50                  55                  60

Leu Met Ala Leu Ser Glu Ile Ile Gly Asn Glu Lys Met Leu Met Leu
 65                  70                  75                  80

Lys Glu Ile Lys Asp Ser Gly Ala Asp Pro Glu Gln Ile Glu Asp Met
                 85                  90                  95

Leu Lys Leu Val Val Asp Lys Glu Lys Lys Lys Arg Ile Asp Glu Tyr
            100                 105                 110

Pro Pro Val Cys Arg Lys Ile Tyr Ala Ala Met Asn Glu Arg Arg Lys
        115                 120                 125

Arg Asn Asp His Asn Leu Glu Ser Tyr Phe Gln Thr Tyr Leu Ser Trp
    130                 135                 140

Leu Thr Asp Ala Gln Lys Asp Glu Ile Lys Lys Met Lys Glu Glu Gly
145                 150                 155                 160

Lys Ser Lys Met Asp Ile Gln Lys Lys Ile Phe Asp Tyr Phe Glu Ser
                165                 170                 175

Leu Thr Gly Asp Lys Lys Lys Lys Ala Ala Glu Glu Leu Gln Gly Cys
            180                 185                 190

Arg Met Ala Leu Arg Glu Ile Val Gly Glu Glu Lys Trp Thr Val Leu
        195                 200                 205

Arg Gln Met Lys Asp Ser Ala Thr Pro Lys Glu Leu Ser Met Lys Val
    210                 215                 220

Glu Glu Met Phe Lys Asp Val Ile Asp Lys Asp Lys Lys Glu Lys Ile
225                 230                 235                 240

Asp Glu Tyr Ala Pro Val Cys Arg Lys Ile Phe Ala Val Ile His Glu
                245                 250                 255

Arg Arg Lys Arg Asn Asp His Asn Leu Glu Ser Tyr Phe Gln Thr Tyr
            260                 265                 270

Leu Ser Trp Leu Thr Asp Ala Gln Lys Asp Glu Ile Lys Lys Met Lys
        275                 280                 285

Glu Glu Gly Lys Ser Lys Met Asp Ile Gln Lys Lys Ile Phe Asp Tyr
    290                 295                 300

Phe Glu Ser Leu Thr Gly Asp Lys Lys Lys Lys Ala Ala Glu Glu Leu
305                 310                 315                 320

Gln Gly Cys Arg Met Ala Leu Arg Glu Ile Val Gly Glu Glu Lys Trp
                325                 330                 335

Thr Val Leu Arg Gln Met Lys Asp Ser Ala Thr Pro Lys Glu Leu Ser
            340                 345                 350

Met Lys Val Glu Glu Met Phe Lys Asp Val Ile Asp Lys Asp Lys Lys
        355                 360                 365

Glu Lys Ile Asp Glu Tyr Ala Pro Val Cys Arg Lys Ile Phe Ala Val
    370                 375                 380
```

-continued

```
Ile His Glu Arg Arg Lys Arg
385                 390


<210> SEQ ID NO 12
<211> LENGTH: 393
<212> TYPE: PRT
<213> ORGANISM: Artificial Sequence
<220> FEATURE:
<223> OTHER INFORMATION: Synthetic protein

<400> SEQUENCE: 12

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
             20                  25                  30

Ser Lys Met Asp Ile Gln Lys Lys Ile Phe Asp Tyr Phe Glu Ser Leu
         35                  40                  45

Thr Gly Asp Lys Lys Lys Lys Ala Ala Glu Glu Leu Gln Gly Cys Arg
     50                  55                  60

Met Ala Leu Arg Glu Ile Val Gly Glu Glu Lys Trp Thr Val Leu Arg
 65                  70                  75                  80

Gln Met Lys Asp Ser Ala Thr Pro Lys Glu Leu Ser Met Lys Val Glu
                 85                  90                  95

Glu Met Phe Lys Asp Val Ile Asp Lys Asp Lys Lys Glu Lys Ile Asp
            100                 105                 110

Glu Tyr Ala Pro Val Cys Arg Lys Ile Phe Ala Val Ile His Glu Arg
        115                 120                 125

Arg Lys Arg Asn Asp His Asn Leu Glu Ser Tyr Phe Gln Thr Tyr Leu
    130                 135                 140

Ser Trp Leu Thr Asp Ala Gln Lys Asp Glu Ile Lys Lys Met Lys Glu
145                 150                 155                 160

Glu Gly Lys Ser Lys Met Asp Ile Gln Lys Lys Ile Phe Asp Tyr Phe
                165                 170                 175

Glu Ser Leu Thr Gly Asp Lys Lys Lys Lys Ala Ala Glu Glu Leu Gln
            180                 185                 190

Gly Cys Arg Met Ala Leu Arg Glu Ile Val Gly Glu Glu Lys Trp Thr
        195                 200                 205

Val Met Arg Gln Met Lys Asp Ser Ala Thr Pro Lys Glu Leu Ser Met
    210                 215                 220

Lys Val Glu Glu Met Phe Lys Asp Val Ile Asp Lys Asp Lys Lys Glu
225                 230                 235                 240

Lys Ile Asp Glu Tyr Ala Pro Val Cys Arg Lys Ile Phe Ala Val Ile
                245                 250                 255

His Glu Arg Arg Lys Arg Asn Asp His Asn Leu Glu Ser Tyr Phe Gln
            260                 265                 270

Thr Tyr Leu Ser Trp Leu Thr Asp Ala Gln Lys Asp Glu Ile Lys Lys
        275                 280                 285

Met Lys Glu Glu Gly Lys Ser Lys Met Asp Ile Gln Lys Lys Ile Phe
    290                 295                 300

Asp Tyr Phe Glu Ser Leu Thr Gly Asp Lys Lys Lys Lys Ala Ala Glu
305                 310                 315                 320

Glu Leu Gln Gly Cys Arg Met Ala Leu Arg Glu Ile Val Gly Glu Glu
                325                 330                 335

Lys Trp Thr Val Leu Arg Gln Met Lys Asp Ser Ala Thr Pro Lys Glu
            340                 345                 350
```

-continued

Leu Ser Met Lys Val Glu Glu Met Phe Lys Asp Val Ile Asp Lys Asp
355 360 365

Lys Lys Glu Lys Ile Asp Glu Tyr Ala Pro Val Cys Arg Lys Ile Phe
370 375 380

Ala Val Ile His Glu Arg Arg Lys Arg
385 390

<210> SEQ ID NO 13
<211> LENGTH: 391
<212> TYPE: PRT
<213> ORGANISM: Artificial Sequence
<220> FEATURE:
<223> OTHER INFORMATION: Synthetic protein

<400> SEQUENCE: 13

Asn Asp His Asn Leu Glu Ser Tyr Phe Gln Thr Tyr Leu Ser Trp Leu
1 5 10 15

Thr Asp Ala Gln Lys Asp Glu Ile Lys Lys Met Lys Glu Glu Gly Lys
20 25 30

Ser Lys Met Asp Ile Gln Lys Lys Ile Phe Asp Tyr Phe Glu Ser Leu
35 40 45

Thr Gly Asp Lys Lys Lys Lys Ala Ala Glu Glu Leu Gln Gly Cys Arg
50 55 60

Met Ala Leu Arg Glu Ile Val Gly Glu Glu Lys Trp Thr Val Leu Arg
65 70 75 80

Gln Met Lys Asp Ser Ala Thr Pro Lys Glu Leu Ser Met Lys Val Glu
85 90 95

Glu Met Phe Lys Asp Val Ile Asp Lys Asp Lys Lys Glu Lys Ile Asp
100 105 110

Glu Tyr Ala Pro Val Cys Arg Lys Ile Phe Ala Val Ile His Glu Arg
115 120 125

Arg Lys Arg Asn Asp His Asn Leu Glu Ser Tyr Phe Gln Thr Tyr Leu
130 135 140

Ser Trp Leu Thr Asp Ala Gln Lys Asp Glu Ile Lys Lys Met Lys Glu
145 150 155 160

Glu Gly Lys Ser Lys Met Asp Ile Gln Lys Lys Ile Phe Asp Tyr Phe
165 170 175

Glu Ser Leu Thr Gly Asp Lys Lys Lys Lys Ala Ala Glu Glu Leu Gln
180 185 190

Gly Cys Arg Met Ala Leu Arg Glu Ile Val Gly Glu Glu Lys Trp Thr
195 200 205

Val Leu Arg Gln Met Lys Asp Ser Ala Thr Pro Lys Glu Leu Ser Met
210 215 220

Lys Val Glu Glu Met Phe Lys Asp Val Ile Asp Lys Asp Lys Lys Glu
225 230 235 240

Lys Ile Asp Glu Tyr Ala Pro Val Cys Arg Lys Ile Phe Ala Val Ile
245 250 255

His Glu Arg Arg Lys Arg Asn Asp His Asn Leu Glu Ser Tyr Phe Gln
260 265 270

Thr Tyr Leu Ser Trp Leu Thr Asp Ala Gln Lys Asp Glu Ile Lys Lys
275 280 285

Met Lys Glu Glu Gly Lys Ser Lys Met Asp Ile Gln Lys Lys Ile Phe
290 295 300

Asp Tyr Phe Glu Ser Leu Thr Gly Asp Lys Lys Lys Lys Ala Ala Glu
305 310 315 320

-continued

```
Glu Leu Gln Gln Gly Cys Leu Met Ala Leu Ser Glu Ile Ile Gly Asn
                325                 330                 335

Glu Lys Met Leu Met Leu Lys Glu Ile Lys Asp Ser Gly Ala Asp Pro
            340                 345                 350

Glu Gln Ile Glu Asp Met Leu Lys Leu Val Val Asp Lys Glu Lys Lys
        355                 360                 365

Lys Arg Ile Asp Glu Tyr Pro Pro Val Cys Arg Lys Ile Tyr Ala Ala
    370                 375                 380

Met Asn Glu Arg Arg Lys Arg
385                 390


<210> SEQ ID NO 14
<211> LENGTH: 389
<212> TYPE: PRT
<213> ORGANISM: Artificial Sequence
<220> FEATURE:
<223> OTHER INFORMATION: Synthetic protein

<400> SEQUENCE: 14

Asn Asp His Asn Leu Glu Ser Tyr Phe Gln Thr Tyr Leu Ser Trp Leu
  1               5                  10                  15

Thr Asp Ala Gln Lys Asp Glu Ile Lys Lys Met Lys Glu Glu Gly Lys
             20                  25                  30

Ser Lys Met Asp Ile Gln Lys Lys Ile Phe Asp Tyr Phe Glu Ser Leu
         35                  40                  45

Thr Gly Asp Lys Lys Lys Lys Ala Ala Glu Glu Leu Gln Gly Cys Arg
     50                  55                  60

Met Ala Leu Arg Glu Ile Val Gly Glu Glu Lys Trp Thr Val Leu Arg
 65                  70                  75                  80

Gln Met Lys Asp Ser Ala Thr Pro Lys Glu Leu Ser Met Lys Val Glu
                 85                  90                  95

Glu Met Phe Lys Asp Val Ile Asp Lys Asp Lys Lys Glu Lys Ile Asp
            100                 105                 110

Glu Tyr Ala Pro Val Cys Arg Lys Ile Phe Ala Val Ile His Glu Arg
        115                 120                 125

Arg Lys Arg Asn Asp His Asn Leu Glu Ser Tyr Phe Gln Thr Tyr Leu
    130                 135                 140

Ser Trp Leu Thr Asp Ala Gln Lys Asp Glu Ile Lys Lys Met Lys Glu
145                 150                 155                 160

Glu Gly Lys Ser Lys Met Asp Ile Gln Lys Lys Ile Phe Asp Tyr Phe
                165                 170                 175

Glu Ser Leu Thr Gly Asp Lys Lys Lys Lys Ala Ala Glu Glu Leu Gln
            180                 185                 190

Gln Gly Cys Leu Met Ala Leu Ser Glu Ile Ile Gly Asn Glu Lys Met
        195                 200                 205

Leu Met Leu Lys Glu Ile Lys Asp Ser Gly Ala Asp Pro Glu Gln Ile
    210                 215                 220

Glu Asp Met Leu Lys Leu Val Val Asp Lys Glu Lys Lys Lys Arg Ile
225                 230                 235                 240

Asp Glu Tyr Pro Pro Val Cys Arg Lys Ile Tyr Ala Ala Met Asn Glu
                245                 250                 255

Arg Arg Lys Arg Asn Asp His Asn Leu Glu Ser Tyr Phe Gln Thr Tyr
            260                 265                 270

Leu Ser Trp Leu Thr Asp Ala Gln Lys Asp Glu Ile Lys Lys Met Lys
        275                 280                 285
```

-continued

Glu Glu Gly Lys Ser Lys Met Asp Ile Gln Lys Lys Ile Phe Asp Tyr
290 295 300

Phe Glu Ser Leu Thr Gly Asp Lys Lys Lys Lys Ala Ala Glu Glu Leu
305 310 315 320

Gln Gln Gly Cys Leu Met Ala Leu Ser Glu Ile Ile Gly Asn Glu Lys
325 330 335

Met Leu Met Leu Lys Glu Ile Lys Asp Ser Gly Ala Asp Pro Glu Gln
340 345 350

Ile Glu Asp Met Leu Lys Leu Val Val Asp Lys Glu Lys Lys Lys Arg
355 360 365

Ile Asp Glu Tyr Pro Pro Val Cys Arg Lys Ile Tyr Ala Ala Met Asn
370 375 380

Glu Arg Arg Lys Arg
385

<210> SEQ ID NO 15
<211> LENGTH: 61
<212> TYPE: PRT
<213> ORGANISM: Artificial Sequence
<220> FEATURE:
<223> OTHER INFORMATION: Synthetic protein

<400> SEQUENCE: 15

Asn Asp His Asn Leu Glu Ser Tyr Phe Gln Thr Tyr Leu Ser Trp Leu
1 5 10 15

Thr Asp Ala Gln Lys Asp Glu Ile Lys Lys Met Lys Glu Glu Gly Lys
20 25 30

Ser Lys Met Asp Ile Gln Lys Lys Ile Phe Asp Tyr Phe Glu Ser Leu
35 40 45

Thr Gly Asp Lys Lys Lys Lys Ala Ala Glu Glu Leu Gln
50 55 60

<210> SEQ ID NO 16
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 16
gcatatgaat gatcataatt tagaaagc 28

<210> SEQ ID NO 17
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 17
ctaaaggatc ctatcaccgc ttacgccgtt cattcattg 39

<210> SEQ ID NO 18
<211> LENGTH: 39
<212> TYPE: DNA

-continued

```
<213> ORGANISM: Artificial Sequence
<220> FEATURE:
<223> OTHER INFORMATION: Synthetic oligonucleotide

<400> SEQUENCE: 18

ctaaaggatc ctatcaccgc ttacgccttt catgtatca                          39
```